US009241998B2

(12) United States Patent
Bose et al.

(10) Patent No.: US 9,241,998 B2
(45) Date of Patent: Jan. 26, 2016

(54) METHODS AND COMPOSITIONS FOR TREATMENT OF CANCER USING ONCOLYTIC RSV ACTIVITY

(75) Inventors: Santanu Bose, Helotes, TX (US); Bandana Chatterjee, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1285 days.

(21) Appl. No.: 12/601,030

(22) PCT Filed: May 21, 2008

(86) PCT No.: PCT/US2008/006499

§ 371 (c)(1), (2), (4) Date: May 10, 2010

(87) PCT Pub. No.: WO2008/144067

PCT Pub. Date: Nov. 27, 2008

(65) Prior Publication Data

US 2010/0303839 A1 Dec. 2, 2010

Related U.S. Application Data

(60) Provisional application No. 61/931,029, filed on May 21, 2007.

(51) Int. Cl.

| | |
|---|---|
| ***A61P 35/00*** | (2006.01) |
| ***A61P 35/04*** | (2006.01) |
| ***A61K 45/06*** | (2006.01) |
| ***A61K 38/19*** | (2006.01) |
| ***A61K 38/20*** | (2006.01) |
| ***A61K 38/45*** | (2006.01) |
| ***A61K 39/155*** | (2006.01) |
| ***C07K 14/535*** | (2006.01) |
| ***A61K 38/17*** | (2006.01) |
| ***A61K 35/768*** | (2015.01) |
| ***A61K 39/12*** | (2006.01) |
| *A61K 38/00* | (2006.01) |

(52) U.S. Cl.

CPC ............... *A61K 45/06* (2013.01); *A61K 35/768* (2013.01); *A61K 38/177* (2013.01); *A61K 38/19* (2013.01); *A61K 38/208* (2013.01); *A61K 38/45* (2013.01); *A61K 39/12* (2013.01); *A61K 39/155* (2013.01); *C07K 14/535* (2013.01); *A61K 38/00* (2013.01); *C12N 2760/18532* (2013.01)

(58) Field of Classification Search

None

See application file for complete search history.

(56) References Cited

U.S. PATENT DOCUMENTS

| | | | | |
|---|---|---|---|---|
| 6,406,693 | B1 | 6/2002 | Thorpe et al. | |
| 6,573,079 | B1 | 6/2003 | Palese et al. | |
| 6,669,943 | B1 | 12/2003 | Palese et al. | |
| 6,689,600 | B1 | 2/2004 | Wu et al. | |
| 6,750,206 | B2 | 6/2004 | Russell et al. | |
| 6,852,522 | B1 | 2/2005 | Palese et al. | |
| 6,896,881 | B1 * | 5/2005 | Russell et al. | 424/93.2 |
| 6,902,743 | B1 | 6/2005 | Setterstrom et al. | |
| 6,902,745 | B2 | 6/2005 | Lee et al. | |
| 7,056,689 | B1 | 6/2006 | Lorence et al. | |
| 7,109,029 | B2 | 9/2006 | Clarke et al. | |
| 7,118,740 | B1 | 10/2006 | Russell et al. | |
| 7,122,182 | B2 | 10/2006 | Groene et al. | |
| 2002/0132769 | A1 | 9/2002 | Kaleko et al. | |
| 2002/0168717 | A1 | 11/2002 | Soppet et al. | |
| 2003/0044384 | A1 | 3/2003 | Roberts et al. | |
| 2003/0077819 | A1 | 4/2003 | Groene et al. | |
| 2003/0095947 | A1 | 5/2003 | Russell et al. | |
| 2003/0165465 | A1 | 9/2003 | Roberts et al. | |
| 2003/0187245 | A1 | 10/2003 | Seifart et al. | |
| 2004/0029112 | A1 | 2/2004 | Thompson et al. | |
| 2004/0091458 | A1 | 5/2004 | Morris et al. | |
| 2004/0091463 | A1 | 5/2004 | Morris et al. | |
| 2004/0109877 | A1 | 6/2004 | Palese et al. | |
| 2004/0115170 | A1 | 6/2004 | Brown et al. | |
| 2004/0209800 | A1 | 10/2004 | Mushinski et al. | |
| 2004/0253214 | A1 | 12/2004 | Russell et al. | |
| 2005/0019308 | A1 | 1/2005 | Norman et al. | |
| 2005/0031643 | A1 | 2/2005 | Szalay et al. | |
| 2005/0048030 | A1 * | 3/2005 | Pickles et al. | 424/93.2 |
| 2005/0054074 | A1 | 3/2005 | Palese et al. | |
| 2005/0112088 | A1 | 5/2005 | Zhao et al. | |
| 2005/0201936 | A1 | 9/2005 | Wold et al. | |
| 2005/0208024 | A1 | 9/2005 | Groene et al. | |
| 2005/0214218 | A1 | 9/2005 | Russell et al. | |
| 2005/0214224 | A1 | 9/2005 | Weers et al. | |
| 2005/0260601 | A1 | 11/2005 | Whitt et al. | |
| 2005/0261232 | A1 | 11/2005 | Strong et al. | |
| 2006/0051335 | A1 | 3/2006 | Russell et al. | |
| 2006/0051370 | A1 | 3/2006 | Szalay et al. | |
| 2006/0127981 | A1 | 6/2006 | Bergman et al. | |
| 2006/0134610 | A1 | 6/2006 | Palese et al. | |
| 2006/0228404 | A1 | 10/2006 | Anderson et al. | |
| 2006/0275262 | A1 | 12/2006 | Mathis et al. | |
| 2007/0025981 | A1 | 2/2007 | Szalay et al. | |

(Continued)

OTHER PUBLICATIONS

Kotelkin et al., J of Virology 2003, vol. 77, pp. 9156-9172.*

Thirukkumaran et al., Cancer Res 2010 vol. 70, pp. 2435-2444.*

Bell et al. "Oncolytic Viruses: Programmable Tumour Hunters" *Curr. Gene Ther*. 2(2):243254 (2002) (Abstract).

Bian et al. "Selective Gene Transfer to Tumor Cells by Recombinant Newcastle Disease Virus via a Bispecific Fusion Protein" *Int. J. Oncol*. 26(2):431-439 (2005) (Abstract).

(Continued)

*Primary Examiner* — Mary E Mosher

*Assistant Examiner* — Myron Hill

(74) *Attorney, Agent, or Firm* — Myers Bigel Sibley & Sajovec, P.A.

(57) ABSTRACT

The present invention relates generally to methods and compositions employing the oncolytic activity of respiratory syncytial virus (RSV) to treat cancer and other neoplastic disorders.

35 Claims, 5 Drawing Sheets

(56) References Cited

U.S. PATENT DOCUMENTS

| | | | |
|---|---|---|---|
| 2007/0031342 | A1 | 2/2007 | Tzannis et al. |
| 2007/0036721 | A1 | 2/2007 | Zinn et al. |

OTHER PUBLICATIONS

Bose et al. "Polarity of Human Parainfluenza Virus Type 3 Infection in Polarized Human Lung Epithelial A549 Cells: Role of Microfilament and Microtubule" *Journal of Virology* 75(4):1984-1989 (2001).
Bose et al. "Temporal Activation of NF-*k*B Regulates an Interferon-Independent Innate Antiviral Response Against Cytoplasmic RNA Viruses" *PNAS* 100(19):10890-10895 (2003).
Bose et al. "Role of Nucleolin in Human Parainfluenza Virus Type 3 Infection of Human Lung Epithelial Cells" *Journal of Virology* 78(15):8146-8158 (2004).
Bitko et al. "An Endoplasmic Reticulum-Specific Stress-Activated Caspase (Caspase-12) is Implicated in the Apoptosis of A549 Epithelial Cells by Respiratory Syncytial Virus" *Journal of Cellular Biochemistry* 80:441-454 (2001).
Cathomen et al. "Preferential Initiation at the Second AUG of the Measles Virus F mRNA: A Role for the Long Untranslated Region" *Virology* 214:628-632 (1995).
Echchgadda et al. "Oncolytic Targeting of Androgen-Sensitive Prostate Tumor by the Respiratory Syncytial Virus (RSV): Consequences of Deficient Interferon-Dependent Antiviral Defense" *BMC Cancer*11 (43): 1-18 (2011).
Echchgadda et al. "Anti-Cancer Oncolytic Activity of Respiratory Syncytial Virus" *Cancer Gene Ther*. 16(12):923(2009).
Elankumaran et al. "Newcastle Disease Virus Exerts Oncolysis by Both Intrinsic and Extrinsic Caspase-Dependent Pathways of Cell Death" *Journal of Virology* 80(15):7522-7534 (2006).
Frigo et al. "Xenobiotic-Induced TNF-α Expression and Apoptosis Through the p38 MAPK Signaling Pathway" *Toxicology Letters* 155:227-238 (2005).
Hallak et al. "Iduronic Acid-Containing Glycosaminoglycans on Target Cells are Required for Efficient Respiratory Syncytial Virus Infection" *Virology* 271:264-275 (2000).
Hara et al. "Antitumor Effect of Gefitinib ('Iressa') on Esophageal Squamous Cell Carcinoma Cell Lines in vitro and in vivo" *Cancer Letters* 226:37-47 (2005).
Jiang et al. "Autocrine Regulation and Experimental Modulation of Interleukin-6 Expression by Human Pulmonary Epithelial Cells Infected with Respiratory Syncytial Virus" *Journal of Virology* 72(3):2496-2499 (1998).
Johnson et al, "Isolation and Characterization of Mouse Probasin: An Androgen-Regulated Protein Specifically Expressed in the Differentiated Prostate" *The Prostate* 43:255-262 (2000).
Jounaidi et al. "Use of Replication-Conditional Adenovirus as a Helper System to Enhance Delivery of P450 Prodrug-Activation Genes for Cancer Therapy" *Cancer Research* 64:292-303 (2004).
Kang et al. "Estrogen Receptor-Independent Inhibition of Tumor Necrosis Factor-α Gene Expression by Phytoestrogen Equol is Mediated by Blocking Nuclear Factor-κActivation in Mouse Macrophages" *Biochemical Pharmacology* 71:136-143 (2005).
Kim et al. "Potentiation of FAS- and Trail-Mediated Apoptosis by IFN-γ in A549 Lung Epithelial Cells: Enhancement of Caspase-8 Expression Through IFN-Response Element" *Cytokine* 20(6):283-288 (2002).
Murphy et al. "Live-Attenuated Virus Vaccines for Respiratory Syncytial and Parainfluenza Viruses: Applications of Reverse Genetics" *J. Clin. Invest*. 110:21-37 (2002).
Muruganandham et al. "Metabolic Signatures Associated with a NAD Synthesis Inhibitor-Induced Tumor Apoptosis Identified by $^{1}$H-Decoupled-$^{31}$P Magnetic Resonance Spectroscopy" *Clin. Cancer Res*. 11(9):3503-3513 (2005).
Naderi et al. "*BEX2* is Overexpressed in a Subset of Primary Breast Cancers and Mediates Nerve Growth Factor/Nuclear Factor-κInhibition of Apoptosis in Breast Cancer Cell Lines" *Cancer Res*. 67(14):6725-6736 (2007).
Orlandi et al. "Propionyl-L-Carnitine Reduces Proliferation and Potentiates Bax-Related Apoptosis of Aortic Intimal Smooth Muscle Cells by Modulating Nuclear Factor-κActivity" *The Journal of Biological Chemistry* 282(7):4932-4942 (2007).
Parks et al. "Controlled Cell Killing by a Recombinant Nonsegmented Negative-Strand RNA Virus" *Virology* 293(1):192-203 (2002) (Abstract).
Pauwels et al. "Rapid and Automated Tetrazolium-Based Colorimetric Assay for the Detection of Anti-HIV Compounds" *Journal of Virological Methods* 20:309-321 (1988).
Peng et al. "Nanoparticulate Delivery of Suicide DNA to Murine Prostate and Prostate Tumors" *The Prostate* 67:855-862 (2007).
Phuangsab et al. "Newcastle Disease Virus Therapy of Human Tumor Xenografts: Antitumor Effects of Local or Systemic Administration" *Cancer Letters* 172:27-36 (2001).
Pridgen et al. "Biodegradable, Polymeric Nanoparticle Delivery Systems for Cancer Therapy" *Nanomedicine* (Lond) 2(5):669-680 (2007) (Abstract).
Sinkovics "Oncogenes-Antioncogenes and Virus Therapy of Cancer" *Anticancer Res*. 9(5):1281-1290 (1989) (Abstract).
Soldani et al, "Poly(ADP-ribose) Polymerase-1 Cleavage During Apoptosis: An Update" *Apoptosis* 7:321-328 (2002).
Springfeld et al. "Envelope Targeting: Hemagglutinin Attachment Specificity Rather than Fusion Protein Cleavage-Activation Restricts *Tupaia Paramyxovirus* Tropism" *Journal of Virology* 79(16):10155-10163 (2005).
Szeberenyi et al. "Newcastle Disease Virus-Induced Apoptosis in PC12 Pheochromocytoma Cells" *American Journal of Therapeutics* 10:282-288 (2003).
Szegezdi et al. "Capase-12 and ER-Stress-Mediated Apoptosis the Story So Far" *Ann. N.Y. Acad. Sci*. 1010:186-194 (2003).
Techaarpornkul et al. "Functional Analysis of Recombinant Respiratory Syncytial Virus Deletion Mutants Lacking the Small Hydrophobic and/or Attachment Glycoprotein Gene" *Journal of Virology* 75(15):6825-6834 (2001).
Teng et al. "Contribution of the Respiratory Syncytial Virus G Glycoprotein and its Secreted and Membrane-Bound Forms to Virus Replication in Vitro and in Vivo" *Virology* 289:283-296 (2001).
Ulane et al. "STAT3 Ubiquitylation and Degradation by Mumps Virus Suppress Cytokine and Oncogene Signaling" *Journal of Virology* 77(11):6385-6393 (2003).
PCT International Preliminary Report on Patentability mailed Dec. 3, 2009 for International Application No. PCT/US2008/006499 (9 pages).
International Search Report and Written Opinion for International Application No. PCT/US2008/06499, dated Aug. 15, 2008 (12 pages).
Baselga et al. "Recombinant Humanized Anti-HER2 Antibody (Herceptin™) Enhances the Antitumor Activity of Paclitaxel and Doxorubicin Against HER2/*neu* Overexpressing Human Breast Cancer Xenografts" *Cancer Research* 58:2825-2831 (1998).
Boccadoro et al. "Preclinical Evaluation of the Proteasome Inhibitor Bortezomib in Cancer Therapy" *Cancer Cell International* 5(18):1-9 (2005).
Davis et al. "Regional Effects of an Antivascular Endothelial Growth Factor Receptor Monoclonal Antibody on Receptor Phoshorylation and Apoptosis in Human 253J B-V Bladder Cancer Xenografts" *Cancer Research* 64:4601-4610 (2004).
Hurwitz et al. "Bevacizumab Plus Irinotecan, Fluorouracil, and Leucovorin for Metastatic Colorectal Cancer" *The New England Journal of Medicine* 350(23):2335-2342 (2004).
Mateos et al. "Bortezomib Plus Melphalan and Prednisone in Elderly Untreated Patients with Multiple Myeloma: Results of a Multicenter Phase 1/2 Study" *Blood* 108(7):2165-2172 (2006).
Mitsiades et al. "The Proteasome Inhibitor PS-341 Potentiates Sensitivity of Multiple Myeloma Cells to Conventional Chemotherapeutic Agents: Therapeutic Applications" *Blood* 101(6):2377-2380 (2003).
Sporn et al. "Weekly Paclitaxel Plus Herceptin in Metastatic Breast Cancer Patients who Relapse After Stem-Cell Transplant" *Annals of Oncology* 10:1259-1260 (1999).
Tran et al. "Development of a Second-Generation Antiandrogen for Treatment of Advanced Prostate Cancer" *Science* 324(5928):787-790 (2009).
Yang et al. "A Randomized Trial of Bevacizumab an Anti-Vascular Endothelial Growth Factor Antibody, for Metastatic Renal Cancer" *The New England Journal of Medicine* 349(5):427-434 (2003).

* cited by examiner

FIGURE 5

METHODS AND COMPOSITIONS FOR TREATMENT OF CANCER USING ONCOLYTIC RSV ACTIVITY

STATEMENT OF PRIORITY

This application is a 35 U.S.C. §371 national phase application of International Application Serial No. PCT/US2008/006499, filed May 21, 2008, which claims the benefit, under 35 U.S.C. §119(e), of U.S. Provisional Application No. 60/931,029, filed May 21, 2007, the entire contents of each of which are incorporated herein by reference.

STATEMENT OF GOVERNMENT SUPPORT

This invention was made with government support under Grant No. AG019660 awarded by the National Institutes of Health. The U.S. Government has certain rights in the invention.

FIELD OF THE INVENTION

The present invention relates generally to methods of treating cancer and other neoproliferative disorders by employing the oncolytic activity of respiratory syncytial virus (RSV) in various methods and compositions provided herein.

BACKGROUND OF THE INVENTION

Oncolytic virotherapy is a bio-therapeutic platform for cancer treatment based on selective infection and killing of cancer cells by oncolytic viruses. Oncolytic viruses are replicating micro-organisms that show tissue tropism during infection of tumors and grow to increased levels in tumor cells relative to normal cells. Due to the enhanced viral burden in tumor cells (but not in normal cells) after infection, the cancer cells are subsequently killed by necrosis or apoptosis.

Some oncolytic viruses (both DNA and RNA viruses) have been identified to date, namely adenovirus, reovirus, herpes simplex virus (HSV), Newcastle disease virus (NDV), vaccinia virus, measles virus, coxsackievirus, and vesicular stomatitis virus (VSV).

While oncolytic viruses have been shown to be useful for cancer treatment, there is still a need in the art for the availability of additional oncolytic viruses. Having a repertoire of numerous oncolytic viruses with different modes of action, properties, and strategies to kill tumor cells of various tissue origins is desirable to thoroughly and effectively treat cancer. Identification of new oncolytic viruses is therefore useful to ensure the ability to efficiently target and kill a variety of tumors originating from various tissues. In addition, the combined use of different classes of oncolytic viruses for cancer therapy (multi-virotherapy) is an alternate route that can be much more efficacious in some cases than the use of a single virus class. The present invention satisfies this need in the art by providing methods of utilizing the newly identified oncolytic properties of respiratory syncytial virus (RSV) in various methods and compositions to treat cancer and related conditions.

SUMMARY OF THE INVENTION

In one aspect, the invention encompasses a method of treating a neoplasm, cancer, and/or primary cancer in a subject by administering to the subject an oncolytically effective amount of a respiratory syncytial virus (RSV).

In another aspect, the invention encompasses a method of reducing metastasis of a primary cancer and/or reducing tumor size or burden in a subject by administering to the subject an oncolytically effective amount of an RSV.

In another aspect, the invention encompasses a method of inducing apoptosis in a tumor and/or reducing pain caused by a tumor in a subject by administering to the subject an oncolytically effective amount of an RSV.

In another aspect, the invention encompasses a method of delivering RSV to a tumor cell in a subject by administering a genetically altered recombinant RSV to the subject, wherein the recombinant RSV comprises one or more nucleotide sequences encoding a protein that specifically binds a tumor-specific antigen and/or tumor-specific protein on the tumor cell.

In another aspect, the invention encompasses a method of increasing the sensitivity of a tumor cell to radiation, chemotherapy, and/or an immune response by infecting the tumor cell with RSV.

In another aspect, the invention encompasses a method of treating a tumor, cancer, and/or neoplasm in a subject by removing the tumor, cancer, and/or neoplasm (e.g., surgically) and administering to the subject an oncolytic amount of RSV.

In another aspect, the invention encompasses a method of eliminating or reducing the number of neoplastic cells in a population of neoplastic cells and normal cells by contacting the population with RSV under conditions whereby RSV can infect the cells of the population, resulting in the elimination or reduction in the number of neoplastic cells in the population.

In another aspect, the invention encompasses a method of preparing a cellular composition and/or tissue for transplantation into a subject by contacting the cellular composition and/or tissue with RSV under conditions whereby the RSV can infect the cells and/or tissue and kill neoplastic cells present in the cellular composition and/or tissue, thereby preparing the cellular composition and/or tissue for transplantation into the subject.

In another aspect, the invention encompasses compositions and methods of using an RSV having one or more than one mutation in one or more than one of the NS1, NS2, N, P, M, SH, G, F, M2-1/M2-2, and L genes of the RSV genome. The present invention further encompasses compositions and method of using an RSV having one or more than one nucleotide sequence heterologous to the virus and/or to the cell infected by the RSV of this invention.

In another aspect, the invention encompasses a method of administering to a subject of this invention an immunosuppressive agent, a chemotherapeutic agent, an immunostimulatory agent, radiation, or any combination thereof, before, during and/or after administration of the RSV.

In another aspect, the invention encompasses compositions and a method of administering RSV with one or more than one other oncolytic virus, i.e., that is not RSV. The present invention further encompasses a method of administering RSV with one or more than one other oncolytic virus and an immunosuppressive agent, a chemotherapeutic agent, an immunostimulatory agent, radiation, or any combination thereof, before, during and/or after administration of the RSV and/or other oncolytic virus.

In another aspect, the invention encompasses compositions and a method of treating a cancer in a subject, comprising administering to the subject an effective amount of a vector comprising a nucleotide sequence encoding one more oncolytic proteins of RSV, either alone or in combination with other oncolytic viruses, with vectors encoding oncolytic protein(s) of other oncolytic viruses and/or with an immunosuppressive agent, a chemotherapeutic agent, an immunostimulatory agent and/or radiation, in any combination and in any order.

The present invention further provides a complex comprising: a) an RSV particle, wherein the RSV particle comprises a viral genome lacking a functional RSV gene; and b) a nanoparticle comprising nucleic acid comprising the functional RSV gene under the control of a cell-specific promoter. Also provided herein is a composition comprising the complex of this invention, in a pharmaceutically acceptable carrier. In further aspects of this invention, a method is provided of establishing an RSV infection in a cell, comprising delivering to the cell the complex of this invention. Additionally provided herein is a method of treating cancer in a subject, comprising delivering the complex of this invention to the subject, wherein the tumor cell-specific promoter is active in a tumor cell of the subject, whereby an oncolytic RSV infection is established in the tumor cell of the subject, thereby treating the cancer in the subject.

Furthermore, the present invention provides a method of inducing tumor cell-specific apoptosis in a subject, comprising delivering the complex of this invention to the subject, wherein the tumor cell-specific promoter is active in a tumor cell of the subject, whereby an oncolytic RSV infection is established in the tumor cell of the subject, thereby inducing tumor cell-specific apoptosis in the subject. In addition, the present invention provides a method of making the complex of this invention, comprising linking the RSV particle as described herein with the nanoparticle as described herein.

Further aspects of this invention include a nanoparticle comprising a nucleic acid encoding a viral protein under the direction of a cell-specific promoter.

Other aspects of the invention are provided in the following brief description of the drawings and detailed description of embodiments of the invention.

BRIEF DESCRIPTION OF THE DRAWINGS

FIGS. 3A-B. Tumor regression caused by intra-tumorally administered RSV. Tumor xenografts in nude mice produced by injected PC-3 cells were examined. A. The effect of tumor growth in mice harboring the tumor xenograft below the ear. B. The effect of tumor growth in mice harboring the tumor xenograft in the dorsal flank. Tumors were allowed to develop and at day 18 (for A) or day 15 (for B), RSV injection was initiated. Injection was given every 2 days for the period shown in the plot. Data shown are mean (n=4). There was no significant difference in tumor volumes among control mice. Tumor volumes among RSV injected mice were also similar.

FIG. 4. Inhibition of tumor growth in nude mice following intra-peritoneal (i.p.) injection of RSV. The rate of tumor regression (tumor grown below the ear) in intra-peritoneal injected mice is shown. RSV injection started at day 18, post implantation of PC-3 cells. Data shown are mean (n=4). No significant difference was found in tumor volumes among control mice. Tumor volumes among RSV injected mice were also similar.

Figure 5:
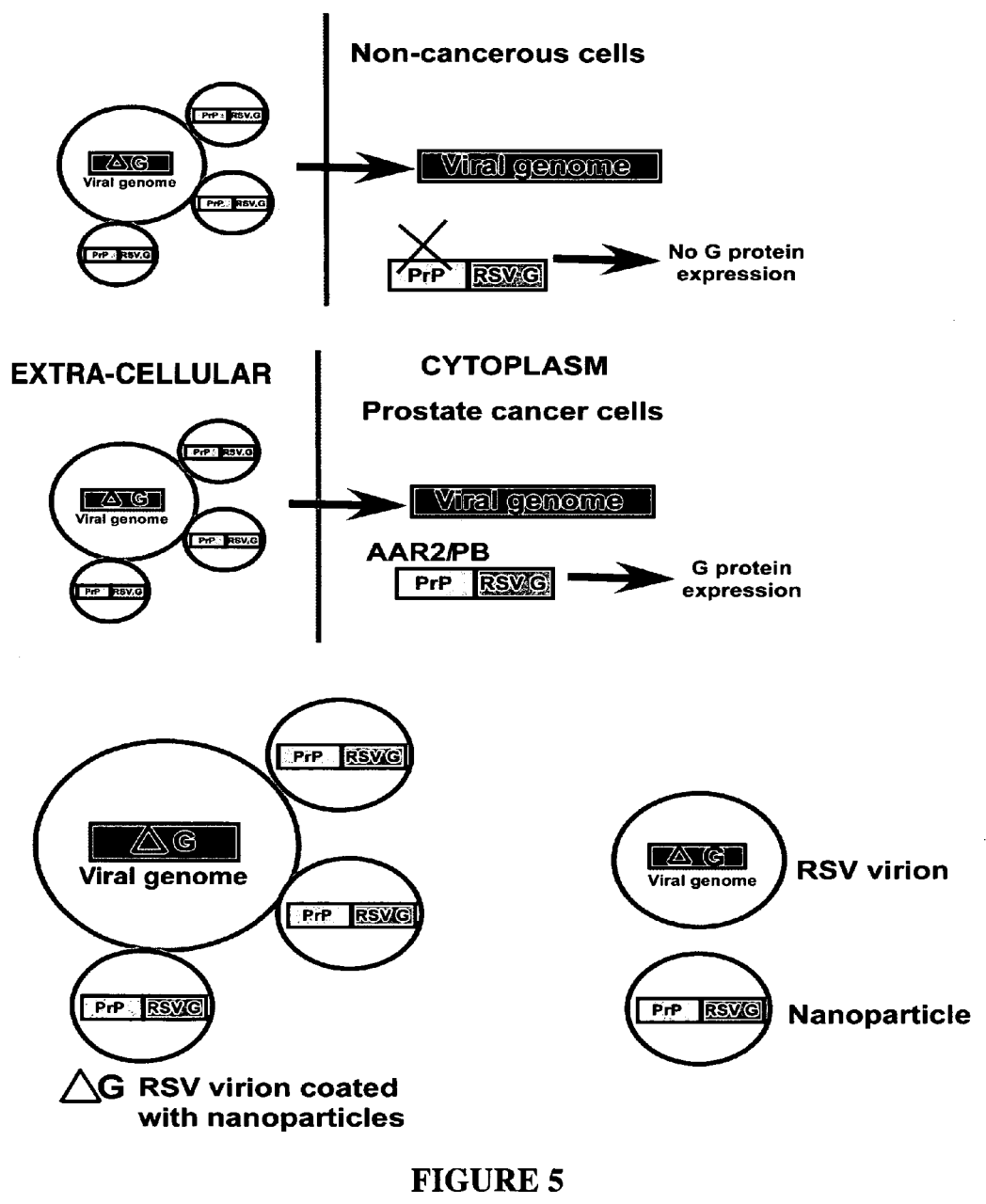

FIG. 5. Selective targeting of recombinant RSV to prostate tumor. Genetically modified RSV devoid of functional G protein/gene (ΔG) is complexed with nanoparticles complexed with nucleic acid encoding RSV G under the control of a prostate cell specific promoter (e.g., probasin promoter). Introduction of the nanoparticle-coated virus into normal cells will not yield productive infection due to lack of functional RSV G production. In contrast, probasin-dependent expression of G protein in prostate tumor cells will result n robust virus growth and oncolysis. PrP: probasin promoter; AAR2/PB: androgen bound androgen receptor that transactivates the probasin promoter in prostate cells (e.g., prostate tumor cells).

DETAILED DESCRIPTION OF THE INVENTION

Figure 1:
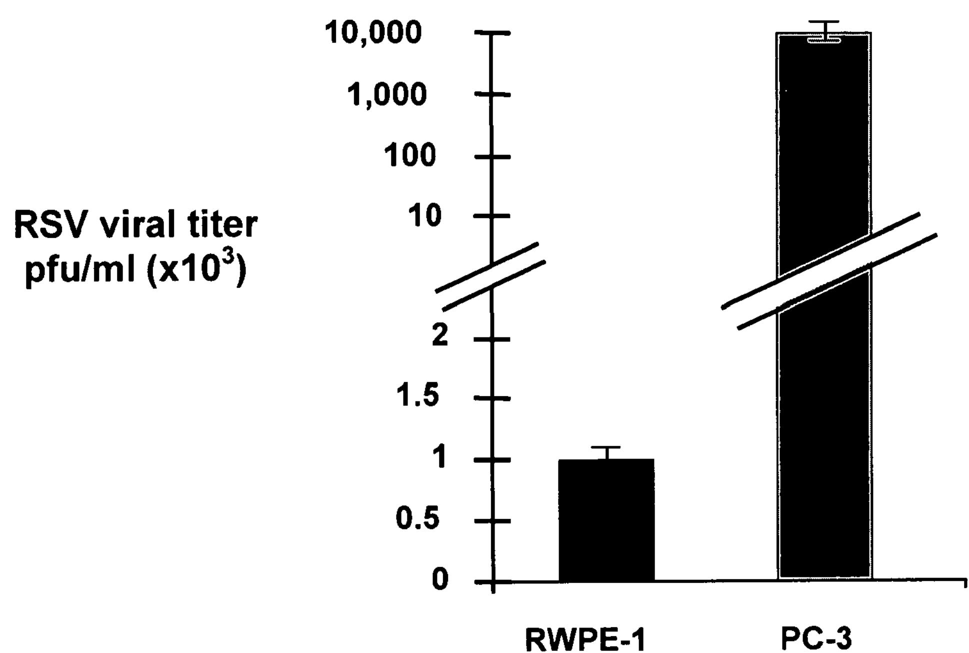
FIG. 1. RSV infectivity in RWPE-1 and PC-3 cells. RSV infection (0.2 MOI) is measured by plaque assay at 36 hours post-infection. Plaque assay values expressed as pfu/ml represent mean±standard deviation for three independent determinations. Standard deviations are shown by the error bars.

The present invention is based on the unexpected discovery that respiratory syncytial virus (RSV) has oncolytic activity. RSV is a non-segmented negative sense single stranded RNA (NNS) virus of the paramyxovirus family that primarily infects the respiratory tract of infants and children to cause mild respiratory disease. Being mildly immunogenic, RSV infection is asymptomatic in adults. The present invention demonstrates that RSV can exert selective anti-cancer activity against human cancer cells. This potent, newly-identified oncolytic function of RSV is useful for developing efficacious virotherapy strategies for treating cancer and other neoplastic disorders in subjects.

Thus, in one embodiment, the invention provides a method of treating a neoplasm and/or neoplastic disorder or condition in a subject by administering to the subject an oncolytically effective amount of a respiratory syncytial virus (RSV), thereby treating the neoplasm and/or neoplastic disorder or condition in the subject.

In a further embodiment, the invention provides a method of treating a cancer and/or a tumor in a subject by administering to the subject an oncolytically effective amount of a respiratory syncytial virus (RSV), thereby treating the cancer and/or tumor in the subject.

In another embodiment, the invention provides a method of reducing tumor size and/or tumor burden in a subject comprising a tumor, comprising administering to the subject an oncolytically effective amount of a respiratory syncytial virus (RSV), thereby reducing tumor size and/or tumor burden in the subject.

As used herein, the term "neoplasm" refers to an abnormal mass of tissue or cells, the division and/or growth of which exceeds and/or is uncoordinated with that of normal tissues or cells, and which persists in the same excessive and/or uncoordinated or uncontrolled manner after cessation of the stimulus which evoked the change to neoplastic growth. Neoplasms may be benign or malignant.

As also used herein, the terms "neoplastic disorder" or "neoplastic condition" describe a disorder or condition, which can be benign or malignant, characterized by uncontrolled and/or unregulated cell division and growth, as would be readily recognized by one of ordinary skill in the art. Nonlimiting examples of neoplastic disorders or neoplastic conditions of this invention include lymphomas, adenocarcinomas, mastocytomas, myelomas, pulmonary cancers, and neoplastic disorders involving macrophages.

"Treat", "treating", or "treatment" refers to any type of action or activity that imparts a modulating effect, which, for example, can be a beneficial effect, to a subject afflicted with a disorder, disease or illness, or at risk of developing a disorder, disease or illness, including improvement in the condition of the subject (e.g., in one or more symptoms), delay in the progression of the condition, prevention or delay of the onset of the disorder, and/or change in clinical parameters, disease or illness, etc., as would be well known in the art.

"Effective amount" refers to an amount of a compound or composition of this invention that is sufficient to produce a desired effect, which can be a therapeutic effect. For example, an "oncolytically effective amount" is an amount of an oncolytic virus or a protein or gene product having oncolytic activity that imparts a therapeutic or beneficial effect in treating a cancer and/or neoplastic disorder or disease in a subject, as well as an amount that results in a reduction in tumor size and/or tumor burden. The exact amount of the composition required for an effective amount will vary from subject to subject, depending on the species, age, weight and general condition of the subject, the severity of the condition being treated, the particular composition used, its mode of administration, the duration of the treatment, the nature of any concurrent treatment, the pharmaceutically acceptable carrier used, and like factors within the knowledge and expertise of those skilled in the art. Thus, it is not possible to specify an exact amount for every composition of this invention. However, an effective amount can be determined by one of ordinary skill in the art in any individual case using only routine experimentation given the teachings herein and by reference to the pertinent texts and literature and/or by using routine experimentation. (See, for example, *Remington: The Science and Practice of Pharmacy,* 21st Edition (2005), Lippincott Williams & Wilkins, Philadelphia, Pa.).

As used herein, the term "cancer" refers to an abnormal proliferation of cells such as a malignant tumor or malignant cell population. Such abnormal proliferation may be in any tissue or organ, free-living in the body (metastasized), or any combination thereof. A cancer of this invention can be, but is not limited to, B cell lymphoma, T cell lymphoma, myeloma, leukemia, hematopoietic neoplasia, thymoma, lymphoma, sarcoma, lung cancer, liver cancer, non-Hodgkin's lymphoma, Hodgkin's lymphoma, adrenal cancer, anal cancer, colorectal cancer, endometrial cancer, esophageal cancer, fallopian tube cancer, gallbladder cancer, gastric cancer, glioblastoma, kidney cancer, laryngeal cancer, medulloblastoma, mesothelioma, neuroblastoma, oropharyngeal cancer, osteosarcoma, parathyroid cancer, thyroid cancer, penile cancer, pituitary cancer, retinoblastoma, rhabdomyosarcoma, urethral cancer, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, testicular cancer, uterine cancer, cervical cancer, vaginal cancer, vulvar cancer, small intestinal cancer, and any other cancer now known or later identified (see, e.g., Rosenberg (1996) *Ann. Rev. Med.* 47:481-491, the entire contents of which are incorporated by reference herein).

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

In another embodiment the invention provides a method of reducing metastasis of a primary cancer in a subject, comprising administering to the subject an oncolytically effective amount of a respiratory syncytial virus (RSV), thereby reducing metastasis of the primary cancer in the subject.

The terms "inhibit," "diminish," "reduce" or "suppress" refer to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified parameter of at least about 5%, 10%, 25%, 35%, 40%, 50%, 60%, 75%, 80%, 90%, 95%, 97%, 98%, 99% or 100%. In particular embodiments, the inhibition or reduction results in little or essentially no detectible activity (at most, an insignificant amount, e.g., less than about 10% or about 5%).

In a further embodiment, the present invention provides a method of reducing tumor size and/or tumor burden in a subject with a tumor, comprising administering to the subject an oncolytically effective amount of RSV, thereby reducing tumor size and/or tumor burden in the subject.

As used herein, the term "tumor" refers to abnormal growth of tissue or cells that can be either malignant or benign. The term includes, but is not limited to, tumors found in prostate, lung, brain, breast, kidney, liver, lung colon, intestines, lymph, muscle, bone, bone marrow, uterus, ovary, vagina, vulva, pancreas, adrenal gland, central nervous system, peripheral nervous system, cervix, bladder, endometrium, throat, esophagus, larynx, thyroid, blood, penal, testicular, thymus, skin, spinal, stomach, anal, bile duct, bowel (colon & rectum), endocrine, eye, ball bladder, bullet (oesophagus) tissues and any combination thereof. Also included are cancers of the head and neck, children's cancers, Kaposi's sarcoma, leukemia (e.g., acute lymphoblastic leukemia, acute myeloid leukemia, chronic lymphocytic leukemia, chronic myeloid leukemia), lymphoma, Hodgkin's lymphoma, non-Hodgkin's lymphoma, melanoma, mesothelioma, myeloma, multiple myeloma, neuroendocrine cancers, soft tissue cancers and sarcomas, as well as cancers of unknown primary origin and any combination thereof.

In another embodiment, the invention provides a method of inducing apoptosis of a tumor cell and/or a neoplastic cell in a subject, comprising administering to the subject an oncolytically effective amount of RSV, thereby inducing apoptosis of a tumor cell and/or neoplastic cell in the subject.

In another embodiment the invention provides a method of reducing pain caused by a tumor and/or neoplastic disorder in a subject, comprising administering to the subject an oncolytically effective amount of RSV, thereby reducing pain caused by the tumor and/or neoplastic disorder in the subject.

In an additional embodiment, the invention provides a method of delivering a respiratory syncytial virus (RSV) to a tumor cell in a subject, comprising administering to the subject a recombinant respiratory syncytial virus (RSV) comprising a heterologous protein that specifically binds a tumor-specific antigen or tumor-specific protein on the tumor cell. Such a recombinant RSV can be genetically modified according to methods well known in the art for manipulating a viral genome, such that a RSV particle of this invention comprises one or more heterologous nucleotide sequences encoding a protein or gene product that imparts tumor cell specific tropism on the RSV particle. Nonlimiting examples of recombinant RSVs that can be employed in the compositions and methods of this invention are described, for example, in U.S. Pat. No. 6,896,881, the entire contents of which are incorporated by reference herein.

A tumor-specific antigen or protein of this invention can include but is not limited to human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), alpha-fetoprotein (AFP), CO17-1A, GA733, gp72, p53, the ras oncogene product, β-HCG, gp43, HSP-70, p17 mel, HSP-70, gp43, HMW, HOJ-1, melanoma gangliosides, TAG-72, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein $p210_{BcR\text{-}ABL}$ and tumor associated viral antigens (e.g., HPV16 E7). In some embodiments, the cancer antigen of this invention can be an antibody produced by a B cell tumor (e.g., B cell lymphoma; B cell leukemia; myeloma; hairy cell leukemia) or a T cell receptor on the surface of a malignant T cell.

In another embodiment the invention provides a method of increasing the sensitivity of a tumor cell in a subject to radiation, comprising infecting the tumor cell in the subject with RSV, thereby increasing the sensitivity of the tumor cell to radiation.

As used herein, the term "radiation" includes, but is not limited to, gamma radiation. For example, for treating curative (radical) cases with radiation, the typical dose for a solid epithelial tumor ranges from about 60 Gy to about 80 Gy, while lymphoma tumors would be treated with about 20 Gy to about 40 Gy. Preventative (adjuvant) doses are typically about 45 Gy to about 60 Gy in about 1.8 Gy to about 2 Gy fractions (for breast, head and neck cancers, respectively).

In another embodiment, the invention provides a method of increasing the sensitivity of a tumor cell in a subject to a chemotherapeutic agent, comprising infecting the tumor cell with RSV, thereby increasing the sensitivity of the tumor cell to a chemotherapeutic agent.

As used herein, the term "chemotherapeutic agent" refers to a chemical substance used to treat cancer and other neoplastic disorders and includes, but is not limited to, antiestrogens, Anthracyclins, Azacitidine, Azathioprine, Bleomycin, Busulfan, Carboplatin, Capecitabine, Cisplatin, Chlorambucil, Cyclophosphamide, Cytarabine, Dacarbazine, Daunorubicin, Docetaxel, Doxifluridine, Doxorubicin, Epirubicin, Epothilone, Etoposide, 5-Fluorouracil, Gemcitabine, Hydroxyurea, Idarubicin, Imatinib, Interferons, Mechlorethamine, Melphalan, Mercaptopurine, Methotrexate, Mitomycin C, Mitoxantrone, Oxaliplatin, Paclitaxel, Pemetrexed, Retinoic acid, Taxol, Taxotere, Tamoxifen, Teniposide, Thiotepa, Tioguanine, Valrubicin, Vinblastine, Vincristine, Vindesine, Vinorelbine, and any combination thereof.

In another embodiment, the invention provides a method of increasing the sensitivity of a tumor cell and/or sensitizing a tumor cell in a subject to an immune response against RSV, comprising infecting the tumor cell with RSV, resulting in the presence of a respiratory syncytial virus antigen on the surface of the infected tumor cell, thereby increasing the sensitivity of the tumor cell and/or sensitizing the tumor cell to an immune response against RSV. By "sensitizing the tumor cell to an immune response again RSV" means to make the tumor cell susceptible to an immune response against RSV by infecting the cell with RSV, wherein the tumor cell would otherwise not be susceptible or would be nonresponsive to an immune response specifically against a RSV antigen.

In another embodiment, the invention provides a method of treating a tumor and/or neoplasm in a subject, comprising removing the tumor and/or neoplasm from the subject (e.g., surgically and/or with radiation and/or with chemotherapy) and administering to the subject an oncolytically effective amount of a respiratory syncytial virus (RSV), thereby treating a tumor and/or neoplasm in the subject. For example, the RSV can be administered to the subject, before, during and/or after the removal of the tumor and/or neoplasm and RSV administration can be continued over a period of hours, days, weeks, months and/or years to control new tumor and/or neoplasm growth in the subject.

In another embodiment, the invention provides a method of reducing the likelihood of recurrence of a tumor and/or neoplasm in a subject, comprising removing the tumor and/or neoplasm from the subject and administering to the subject an oncolytically effective amount of RSV, thereby reducing the likelihood of recurrence of a tumor and/or neoplasm in the subject. As noted above, for example, the RSV can be administered to the subject, before, during and/or after the removal of the tumor and/or neoplasm and RSV administration can be continued over a period of hours, days, weeks, months and/or years to reduce the likelihood of recurrence or even prevent recurrence of the tumor and/or neoplasm in the subject.

In another embodiment, the invention provides a method of eliminating or reducing the number of neoplastic cells in an ex vivo population of neoplastic cells and normal cells, comprising contacting the population with a respiratory syncytial virus (RSV) under conditions whereby the respiratory syncytial virus can infect the cells and kill the neoplastic cells, thereby eliminating or reducing the number of neoplastic cells in the ex vivo population.

In another embodiment the invention provides a method of preparing a cellular composition and/or organ for transplantation into a subject, comprising contacting the cellular composition and/or organ with a respiratory syncytial virus (RSV) under conditions whereby the respiratory syncytial virus can infect the cells of the composition and/or organ and selectively kill neoplastic cells present in the cellular composition and/or organ, thereby preparing the cellular composition and/or organ for transplantation into the subject. In some embodiments, the cellular composition and/or organ can be autologous to the transplant recipient. In other embodiments, the cellular composition and/or organ can be heterologous to the transplant recipient. Nonlimiting examples of cellular compositions for transplantation include bone marrow cells and white blood cells. Nonlimiting examples of an organ for transplantation include kidney, lung, liver, pancreas, etc.

The invention further provides methods of using, and compositions of, a recombinant respiratory syncytial virus, comprising one or more than one mutation in one or more than one RSV gene. Such RSV genes include NS1, NS2, N, P, M, SH, G, F, M2-1/M2-2, and L genes, and any combination thereof. The mutation(s) in the one more RSV genes can be attenuating, and/or can impart a phenotypic change in the tropism and/or infectivity of the RSV particle, as would be known to one of ordinary skill in the art.

In further embodiments, a recombinant RSV of this invention can comprise one or more than one nucleotide sequence heterologous to the virus and/or the tumor cell. A nucleotide sequence that is heterologous to the virus and/or to the cell infected by the virus is a nucleotide sequence that is not normally present in the virus and/or the cell infected by RSV. The heterologous nucleotide sequence can also be a sequence that is introduced into the cell or virus via recombinant technology and is the same or similar to a nucleotide sequence that is endogenous to the virus and/or cell.

The present invention further provides embodiments wherein the RSV can comprise one or more mutations of a RSV gene (including nucleotide deletions, substitutions and/or additions) and can further comprise one or more heterologous nucleotide sequences, in any combination.

Examples of heterologous nucleotide sequences that can be introduced into a RSV genome for use in the compositions and methods of this invention include, but are not limited to, those that encode a protein for a cytolytic agent; cytotoxic agent (such as herpes virus thymidine kinase (TK) used in combination with gancyclovir treatment); apoptotic agent (such as Bax and Bad); antibody (e.g., an anti-anti-RSV antibody); tumor suppressor protein (e.g., p53); cytokine; heterologous antigen expressed on the surface of a tumor cell to elicit an immune response; interferon; anti-angiogenesis agent (e.g., angiostatin, endostatin, and Timps (tissue inhibitors of matrix metalloproteinases)); CTL responsive peptide (e.g., HLA-B*08-restricted RSV specific CTL epitope), an immunostimulatory agent (e.g., human monocyte chemoattractant protein-1 (MCP-1), granulocyte-macrophage colony stimulating factor (GM-CSF), TRAIL (TNF-related apoptosis inducing ligand), and/or an interleukin (e.g., interleukin-12), in any combination.

The invention further provides a method of administering an immunosuppressive agent, a chemotherapeutic agent, an immunostimulatory agent, radiation, or any combination thereof, before, during and/or after administration of any of the compositions of this invention.

Nonlimiting examples of immunosuppressive agents include Azathioprine, Anti-anti-RSV, Alefacept, Anakinra, Anti-lymphocyte globulin, Anti-thymocyte globulin, Ascomycin, Auranofin, Aurothioglucose, Azathioprine, Basiliximab, CNTO 1275, Ciclosporin (Cyclosporine), Cortisol, Cyclic steroids, Daclizumab, Disodium aurothiomalate, Etanercept, Everolimus, Gliotoxin, Gold salts, Gusperimus, Leflunomide, Mercaptopurine, Methotrexate, Mycophenolic acid, Natalizumab, Penicillamine, Pimecrolimus, Prednisone, Rapamycin, Sirolimus, Sodium aurothiomalate, Sulfasalazine, Tacrolimus, natural anti-cancer herbal agents, and any combination thereof.

As used herein, the term "immunostimulatory agent" refers to an agent having immune simulating properties and includes, but is not limited to, immunostimulatory cytokines (e.g., GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules in any combination), oligodeoxynucleotides (ODN), CpG, cytotoxic/apoptotic/suicides genes and proteins (e.g., pro-apoptotic molecules like Bax and Bad; herpes virus thymidine kinase (TK) (e.g., in combination with gancyclovir treatment)), and immuno-stimulatory genes and proteins (e.g., human monocyte chemoattractant protein-1 (MCP-1); granulocyte-macrophage colony stimulating factor (GM-CSF); TRAIL (TNF-related apoptosis inducing ligand); and interleukins (e.g., interleukin-12).

A tumor of this invention can include but is not limited to a hematopoietic cell tumor, primary tumor, metastatic tumor, melanoma tumor, a carcinoma tumor, an epithelioma tumor, a glioma tumor, a myeloma tumor, a leukemia, a lymphoma, an adenocarcinoma, a fibrosarcoma, a melanoma, an osteosarcoma, a synovial sarcoma, a fibrosarcoma, and a neuroblastoma. A tumor can be found, for example, in prostate, lung, brain, breast, kidney, liver, lung colon, intestines, lymph, muscle, bone, bone marrow, uterus, ovary, vagina, vulva, pancreas, adrenal gland, central nervous system, peripheral nervous system, cervix, bladder, endometrium, throat, esophagus, larynx, thyroid, blood, penal, testicular, thymus, skin, spinal, stomach, anal, bile duct, bowel (colon & rectum), endocrine, eye, ball bladder, and gullet (esophagus) tissues, and any combination thereof.

The methods of this invention can be employed to treat and/or reduce the tumor size and/or burden of a tumor having a diameter in the range of about 0.5 cm to about 50 cm. For example, a tumor of this invention can have a diameter of about 0.5, 1.0, 1.5, 2.0, 2.5, 3.0, 3.5, 4.0, 5, 6, 7, 8, 9, 10, 12, 14, 16, 18, 20, 25, 30, 35, 40, 45 or 30 cm, as well as any value within this range not specifically recited herein.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year and/or as necessary to control the condition. The amount and frequency of administration of the composition of this invention will vary depending on the particular condition being treated or to be prevented or controlled and the desired therapeutic effect.

The compositions of this invention can be administered to a cell of a subject either in vivo or ex vivo. For administration to a cell of the subject in vivo, as well as for administration to the subject, the compositions of this invention can be administered, for example as noted above, orally, parenterally (e.g., intravenously), by intramuscular injection, intradermally (e.g., by gene gun), by intraperitoneal injection, subcutaneous injection, intratumorally, transdermally, extracorporeally, topically or the like, in any combination and in any order.

If ex vivo methods are employed, cells or tissues can be removed and maintained outside the body according to standard protocols well known in the art while the compositions of this invention are introduced into the cells or tissues. For example, the compositions of this invention can be introduced into cells via infection, as well as via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells and tissues into a subject.

Administration of the compositions of this invention can be achieved by any one of numerous, well-known approaches, for example, but not limited to, direct administration of the RSV, or an oncolytic RSV protein-encoding nucleic acid in a plasmid or viral vector, and/or in combination with carriers such as, e.g., cationic liposomes. Such methods are well known in the art and readily adaptable for use in the methods described herein. Furthermore, the compositions of this, invention can be used to target certain diseases, tumor types, and/or cell populations by using the targeting characteristics of the carrier, which would be well known to the skilled artisan.

In some embodiments, administration of the RSV and/or other compositions of this invention according to the methods of this invention can be via direct delivery into the tumor and/or on the tumor surface either at a single site or at multiple sites. The compositions of this invention can also be administered or delivered in the proximity of and/or near a tumor or neoplasm. In other embodiments, the RSV and/or other compositions of this invention can be administered systemically according to various routes of administration described herein and as are well known in the art. In yet further embodiments both types of administration, i.e., directly to the tumor and systemically, can be employed.

In the methods of the present invention, a dose of RSV to be administered can be in a range from about $1\times10^{1}$ plaque forming units (pfu) to about $1\times10^{12}$ pfu. Thus, a dose of RSV of this invention can be about $1\times10^{2}$ pfu, about $1\times10^{3}$ pfu, about $1\times10^{4}$ pfu, about $1\times10^{5}$ pfu, about $1\times10^{6}$ pfu, about $1\times10^{7}$ pfu, about $1\times10^{8}$ pfu, $1\times10^{9}$ pfu, about $1\times10^{10}$ pfu, about $1\times10^{11}$ pfu, or about $1\times10^{12}$ pfu, including any value within this range not specifically recited herein.

A subject of the present invention can be any animal susceptible to cancer and/or neoplastic disorders. For example, the subject can be a mammal, which in some embodiments can be a human, nonhuman primate, dog, cat, horse, cattle, livestock, or any other mammalian species. The mouse experimental tumor in vivo assays are also well recognized and accepted as predictive of in vivo activity in other animals such as, but not limited to, humans.

In practicing the present invention the RSV may be a live purified RSV, an attenuated RSV or a combination of both. Furthermore, the RSV can be human RSV bovine RSV, or a combination thereof, as well as any RSV strain now known or later identified.

The methods and compositions of the present invention can include administering one or more than one oncolytic virus other than RSV in combination with RSV and/or a composition of this invention, before, during and/or after administration of the RSV and/or composition. Nonlimiting examples of such oncolytic viruses include nonengineered or engineered adenovirus, reovirus (e.g., Reolysin®), herpesvirus, Newcastle disease virus, vaccinia virus, measles virus, Coxsackie virus, vesicular stomatitis virus, parvovirus, influenza virus, and rabbit myxoma virus, and any combination thereof.

The methods and compositions of the present invention wherein the RSV and RSV compositions of this invention are administered with one or more different oncolytic viruses can further include an immunosuppressive agent, a chemotherapeutic agent, an immunostimulatory agent, radiation, or any combination thereof and in any order.

The methods and compositions of the present invention can include pharmaceutically acceptable carrier. A "pharmaceutically acceptable carrier" is a component such as a salt, carrier, excipient or diluent of a composition that is (i) compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition.

Non-limiting examples of pharmaceutically acceptable components include, without limitation, any of the standard pharmaceutical carriers such as phosphate buffered saline solutions, water, emulsions such as oil/water emulsion, microemulsions and various types of wetting agents. In particular, it is intended that a pharmaceutically acceptable carrier be a sterile carrier that is formulated for administration to or delivery into a subject of this invention. Furthermore, a pharmaceutically acceptable carrier is any carrier molecule approved by a regulatory agency of the Federal or a state government or listed in the U.S. Pharmacopeia or other generally recognized pharmacopeia for use in animals, and more particularly in humans. Such carrier can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Examples of suitable pharmaceutical carriers are well known to those skilled in the art (See, for example, *Remington: The Science and Practice of Pharmacy,* 21$^{st}$ Edition (2005), Lippincott Williams & Wilkins, Philadelphia, Pa.).

Thus, the present invention comprises, consists essentially of and/or consists of a composition comprising a respiratory syncytial virus of this invention in a pharmaceutically acceptable carrier. Also provide herein is a composition comprising a RSV of this invention and one or more than one different oncolytic virus in a pharmaceutically acceptable carrier. Further provided is a RSV of this invention and a chemotherapeutic agent, an immunosuppressive agent and/or an immunostimulatory agent, in any combination, in a pharmaceutically acceptable carrier. Additional embodiments include a composition comprising a RSV of this invention, one or more different oncolytic viruses and a chemotherapeutic agent, an immunosuppressive agent and/or an immunostimulatory agent, in any combination, in a pharmaceutically acceptable carrier.

In yet further embodiments, the present invention provides a kit comprising one or more of the compositions of the present invention and optionally instructions for use and/or administration. It would be well understood by one of ordinary skill in the art that the kits of this invention can comprise one or more containers and/or receptacles to hold the reagents of the kit, along with appropriate buffers and/or solutions and directions for using the kit, as would be well known in the art. For example, a kit of this invention can comprise a RSV of this invention, and/or one or more than one different oncolytic virus of this invention and/or chemotherapeutic, immunosuppressive and/or immunostimulatory agents in any combination. Each of these components of the kit can be combined in the same container and/or provided in separate containers.

In certain embodiments of this invention involving an immune response, the methods and compositions provide herein can include an adjuvant. As used herein, "adjuvant" describes an agent capable of being combined with the compositions of this invention to further enhance an immune response without deleterious effect on a subject or a cell of a subject. Nonlimiting examples of an adjuvant of this invention can be, but are not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L- alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

In another embodiment, the present invention provides a method of treating a cancer in a subject, comprising delivering a heterologous nucleic acid encoding an oncolytic respiratory syncytial virus protein to a tumor cell of the subject, thereby treating the cancer in the subject. An oncolytic RSV protein of this invention can be a protein encoded by, for example, the NS1, NS2, N, P, M, SH, G, F, M2-1/M2-2 and/or L gene of the RSV genome, including any functional variant or mutant thereof, and any combination thereof.

Administration of the nucleic acids of this invention can be achieved by any one of numerous, well-known approaches, including for example, but not limited to, viral infection direct transfer of the nucleic acids, in a plasmid or viral vector, or via transfer in cells or in combination with carriers such as cationic liposomes. Such methods are well known in the art and readily adaptable for use in the methods described herein. Furthermore, these methods can be used to target certain diseases, tumor types, and/or cell populations by using the targeting characteristics of the carrier, which would be well known to the skilled artisan.

Vectors employed in the methods of this invention can be any nucleotide construct used to deliver nucleic acid into cells, e.g., a plasmid or viral vector, such as a retroviral vector which can package a recombinant retroviral genome (see e.g., Pastan et al., *Proc. Natl. Acad. Sci. U.S.A.* 85:4486 (1988); Miller et al., *Mol. Cell. Biol.* 6:2895 (1986)). The recombinant retrovirus can then be used to infect and thereby deliver a nucleic acid of the invention to the infected cells. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naldini et al., *Science* 272:263-267, 1996), pseudotyped retroviral vectors (Agrawal et al., *Exper. Hematol.* 24:738-747, 1996), alphavirus vectors and any other vector system now known or later identified. Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used nucleic acid transfer methods. Appropriate means for transfection, including viral vectors, chemical transfectants, or physico-mechanical methods such as electroporation and direct diffusion of DNA, are described by, for example, Wolff et al., *Science* 247:1465-1468, (1990); and Wolff, *Nature* 352:815-818, (1991).

Furthermore, the nucleic acids of this invention encoding oncolytic RSV proteins can be administered in combination with any of the other compositions of this invention (e.g., a heterologous nucleotide sequence encoding a protein of this invention such as an apoptotic protein, a cytolytic protein, etc., as described herein and/or one or more different oncolytic viruses and/or one or more nucleotide sequences encoding oncolytic proteins of said different oncolytic viruses and/or chemotherapeutic agents, immunosuppressive agents, immunostimulatory agents and/or radiation, in any order and/or combination as described herein).

It is further contemplated that a recombinant or genetically engineered RSV of this invention, as well as a heterologous nucleotide sequence encoding an oncolytic RSV protein can also comprise a tissue-, organ-, and/or tumor-specific promoter and/or transcription factor that allows for the control of RSV gene expression and heterologous gene expression so that it takes place specifically on/in or in the proximity of a desired target cell of this invention, which can be a tumor cell and/or neoplastic cell.

Further provided herein is a method of treating cancer in a subject, comprising administering to the subject a respiratory syncytial virus particle of this invention comprising a mutation in a RSV protein that introduces a cancer-associated protease cleavage site within the RSV particle, resulting in cleavage of the RSV protein only by a cancer- or tumor-associated protease and subsequent infection of tumor cells in proximity to the cancer- or tumor-associated protease.

Thus, in this embodiment, the infectivity of the virus is restricted largely to tumor cells by making its proteolytic activation dependent on a tumor-associated protease. Proteases such as matrix-metalloproteinases (MMPs; e.g., MMP1, MMP2, MMP3, MMP7, MMP9, MMP11, MMP12, MMP14, etc.), plasminogen activator/plasmin system, p65, cathepsins, trypsin-like proteases, human kallikrein 2 and prostate specific antigen are intimately involved in cancer invasion and metastasis and in complement resistance, and tumors therefore provide a protease-rich microenvironment.

The invention thus provides methods and compositions whereby selected cancer associated protease cleavage sites are introduced into RSV. For example, cleavage of the $F_0$ precursor can be made dependent on a protease other than furin by replacement of the furin cleavage signal in RSV with that of the cleavage signal of another protease.

Proteases with sites useful for restricting the infectivity of a therapeutic virus according to the invention are known in the art (see, e.g., U.S. Pat. No. 6,896,881, incorporated by reference herein). The cloning of the measles virus F protein into an expression vector, pCG, under control of the CMV early promoter to generate the plasmid pCG-F was described by Cathomen et al. (1995, *Virology* 214: 628). Site-directed mutagenesis to convert the furin cleavage site to a site for another protease may be accomplished by one of skill in the art using any of a number of site-directed mutagenesis methods known in the art. One example of a site-directed mutagenesis approach is that embodied by the QuikChange Site-Directed Mutagenesis Kit (Stratagene, La Jolla, Calif.).

RSVs of this invention modified to restrict infectivity by changing the furin cleavage site can be assessed for restricted infectivity by infecting cultured cells in the presence and absence of the protease, if it is an extracellular protease. For an intracellular protease associated with a given tumor cell type, cells either expressing or not expressing the protease are infected with recombinant virus. In one embodiment, the infectivity of the virus is considered to be modified if the virus infects (i.e., causes the formation of syncytia or plaques) cells either in the presence of or expressing the specific protease more efficiently than it infects cells either not expressing or in the absence of the specific protease. As used in this context, "more efficiently" or "to a greater degree" refers to a number of syncytia or plaques formed in a given amount of time that is at least 1.25-fold, and preferably 10-fold, 100-fold, 1000-fold or greater in the cells expressing or cultured in the presence of the protease, relative to cells not expressing or not cultured in the presence of the protease.

The present invention additionally provides a complex comprising: a) an RSV particle, wherein the RSV particle comprises a viral genome lacking a functional RSV gene; and b) a nanoparticle comprising nucleic acid comprising the functional RSV gene under the control of a cell-specific promoter. The functional RSV gene that is deleted or disabled in the RSV genome can be any of the RSV genes that make up the RSV genome (e.g., NS1, NS2, N, P, M, SH, G, F, M2-1/M2-2, and L), as well as any combination of these genes. The gene can be deleted completely or partially from the RSV genome and/or the gene can be mutated or altered according to art known methods to yield a gene that is not functional. By "functional" is meant that the gene is transcribed and translated to produce the intended gene product that contributes to infection of a cell by RSV and subsequent production of progeny virions that are infectious. Therefore, the genome lacking one or more than on functional RSV gene can be delivered into a cell but the genome alone is not capable of providing all of the gene products required for a productive RSV infection. The missing functional RSV gene or genes is/are provided by the nanoparticle(s) attached to the RSV virion, the combination of which comprises a complex of this invention.

In some embodiments of the complex of this invention, the functional RSV gene can encode RSV G protein.

In various embodiments of the complex of this invention, the cell-specific promoter can be any cell-specific promoter now known in the art or later identified and in particular embodiments, the cell-specific promoter is active in a cell that can be a tumor cell or a cell that s susceptible to becoming a tumor cell. Non-limiting examples of cell-specific promoters of this invention include promoters specific for cells of the breast (e.g., erbB2 promoter), the liver (e.g., AFP promoter), the pancreas (e.g., CCKAR promoter), the prostate (e.g., prostate-specific antigen (PSA) promoter, a PSMA promoter, kallikrein 2 promoter, PSCA promoter, probasin promoter, and TARP), the skin (e.g., TRP1 promoter for melanoma), the kidneys, etc. Such cell-specific promoters are well known in the art.

In certain embodiments of this invention, the cell-specific promoter of the complex of this invention is a prostate cell-specific promoter, which can be, e.g., a prostate-specific antigen promoter.

Further provided herein is composition comprising the complex of this invention in a pharmaceutically acceptable carrier.

Methods are also provided herein of using the complex of this invention and include, e.g., a method of establishing an RSV infection in a cell, comprising delivering to the cell the complex of this invention.

Additionally provided herein is method of treating cancer in a subject, comprising delivering the complex of this invention to the subject, wherein the tumor cell-specific promoter is active in a tumor cell of the subject, whereby an oncolytic RSV infection is established in the tumor cell of the subject, thereby treating the cancer in the subject.

In yet further embodiments, the present invention provides a method of inducing tumor cell-specific apoptosis in a subject, comprising delivering the complex of this invention to the subject, wherein the tumor cell-specific promoter is active in a tumor cell of the subject, whereby an oncolytic RSV infection is established in the tumor cell of the subject, thereby inducing tumor cell-specific apoptosis in the subject.

The complex of this invention, as well as the nanoparticle of this invention can be delivered to a cell by any of a variety of cell delivery methods, including, e.g., infection by a virus particle, via plasmids, via liposomes, etc., as are well known in the art.

Also provided herein is a nanoparticle comprising a nucleic acid encoding a viral protein under the direction of a cell-specific promoter. In some embodiments, the viral protein can be an RSV protein, which can be, for example, a RSV G protein. In various embodiments, the nanoparticle of this invention can comprise a cell-specific promoter that can be, e.g., a prostate cell-specific promoter.

A nanoparticle of this invention can comprise various materials known in the art for nanoparticles, including but not limited to poly-B-amino ester compounds, such as cationic poly-B-amino ester polymer/C32 and additional compounds as described in the art, e.g., in U.S. Patent Publication No. 2006/0228404 to Anderson et al. entitled "Compositions and methods for treatment of hypertrophic tissues" and published on Oct. 12, 2006, the entire contents of which are incorporated herein for its teachings of nanoparticle composition, production and delivery into cells. Further embodiments of this invention include a method of making the complex of this invention, comprising linking the RSV particle of this invention with the nanoparticle of this invention. Methods for linking nanoparticles to other moieties for complex formation are well known in the art and include, for example, the methods described in Peng et al. ("Nanoparticle delivery of suicide DNA to murine prostate and prostate tumors" *Prostate* 67:855-862 (2007)), the entire contents of which are incorporated herein by reference for its teachings of nanoparticle composition, linking and delivery into cells.

Additional methods useful in practicing the present invention are well known to those skilled in the art. References disclosing such methods include *Molecular Cloning: A Laboratory Manual,* 2d ed., Cold Spring Harbor Laboratory Press, Sambrook et al., eds. (1989) and *Methods in Enzymology: Guide to Molecular Cloning Techniques*, Academic Press, Berger and Kimmel eds. (1987).

The following non-limiting examples are provided to further illustrate the present invention.

EXAMPLES

Example 1

RSV-Mediated Oncolysis of Human Prostate Cancer Cells In Vitro

These studies provide the first identification of oncolytic activity for RSV. This example illustrates that RSV can exert selective anti-cancer activity against PC-3 human prostate cancer cells in vitro in cell culture. The PC-3 cells were originally isolated from bone metastases of a prostate tumor patient. These androgen-insensitive cells are poorly differentiated and highly tumorigenic, showing aggressive migratory (metastasis) behavior in culture and in tumor xenografts grown in nude mice.

RSV (A2 strain) was propagated in CV-1 cells. The viral titer was monitored by plaque assay analysis with CV-1 cells and measured as plaque forming units per milliliter (pfu/ml). RSV at 0.2 or 2 multiplicity of infection (MOI) was then added to RWPE-1 and PC-3 cells obtained from the American Type Culture Collection (ATCC) (Manassas, Va.) for absorption at 37° C. for 1.5 hours. The cells were then washed and the infection was continued for an additional 4 hours to 42 hours. At various post-infection time periods, culture supernatants were collected and measured for virus yield by plaque assay analysis. For some infected cells, the cell morphology was visualized microscopically.

Selective enhanced RSV infectivity of PC-3 prostate cancer cells over RWPE-1 normal prostate cells is shown in FIG. 1, which shows RSV viral titre measured at 36 hours post-infection by plaque assay of PC-3 cancer cells and RWPE-1 non-cancerous cells infected with RSV at 0.2 MOI. RSV infection was dramatically augmented (by 10,000 fold) in PC-3 cells compared to the non-tumorigenic RWPE-1 cells. In RWPE-1 cells the viral titer was 1000 pfu/ml, while in PC-3 cells the titer was $1\times10^7$ pfu/ml. It is noteworthy that at 0.2 MOI, the viral infection occurred at 2 virus particles per 10 cells. This low virus dosage ensured replication and spread of progeny viruses during the infection time-frames. The dosage also mimics an in vivo situation, where a few viral particles infecting the host establish productive infection by spreading among neighboring cells.

In a different experiment, a single-step growth curve, of RSV infection at 2 MOI for 4 hours to 42 hours in PC-3 cancer cells and RWPE-1 non-cancerous cells, also showed much more robust growth of RSV in PC-3 cells compared to RWPE-1 cells. The much greater cytopathic effect of RSV on PC-3 cells compared to RWPE-1 cells (due to dramatically increased viral burden in cancerous PC-3 cells) was shown by a significantly higher cell death, evident from cell rounding and loss of normal cellular morphology when examined microscopically. This dramatic ten thousand fold enhancement of RSV infectivity in the PC-3 human prostate cancer cells compared to the non-tumorigenic RWPE-1 human epithelial cells from the prostate and the associated robust RSV growth in vitro in cancer cells compared to normal cells demonstrated that RSV is an oncolytic virus.

Example 2

RSV-Induced Selective Apoptosis of Human Prostate Cancer Cells in Vitro

Figure 2:
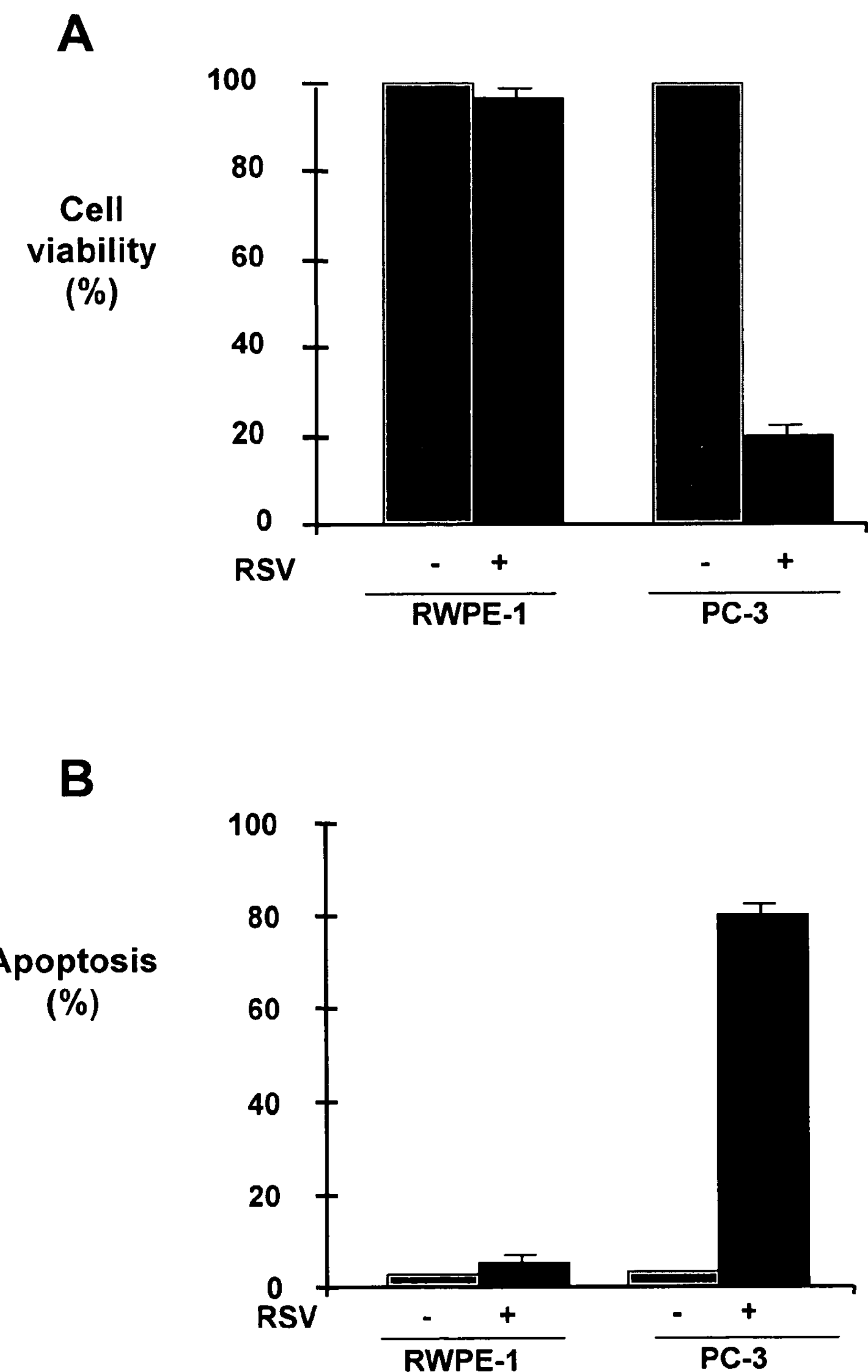
FIGS. 2A-B. Apoptosis and cell viability of RSV infected RWPE and PC-3 cells. A. MTT cell viability assay of cells infected with RSV (0.2 MOI) for 36 hours. MTT assay values are mean±standard deviation of 6 wells and triplicate experiments. Uninfected (−) cells indicate 100% cell viability. B. TUNEL assay results for measurements of apoptosis of RSV (0.2 MOI) infected cells at 36 hours post-infection. Percent (%) apoptotic cells were calculated based on the total number of cells present during each experimental set. Apoptotic values represent mean±SD for three determinations.

This example illustrates that RSV can selectively induce apoptosis of PC-3 human prostate cancer cells in vitro. Cell cytotoxicity of PC-3 and RWPE-1 cells infected with RSV (0.2 MOI) for 36 hours was first quantified by determining the number of viable cells using a tetrazolium-based colorimetric (MTT) assay (see, for example Pauwels R, et al. (1988) *Journal of Virological Methods.* 20: 309-21). The high viral burden in PC-3 cells induced loss of viable PC-3 cells, while RSV infection did not alter cell viability of normal RWPE cells (FIG. 2A).

This loss of cell viability of infected PC-3 cells was confirmed as due to apoptosis. Apoptotic analysis was performed on dissociated cells fixed with cold ethanol and used for TUNEL analysis (see, for example Hara F, et al. (2005) *Cancer Letters.* 226: 37-47) with an in situ cell death detection kit (Roche Applied Science, Indianapolis, Ind.). DNA in apoptotic nuclei incorporated fluorescein-labeled nucleotides and was then analyzed by fluorescence-activated cell sorting (FACS). The TUNEL assay with RSV infected cells (0.2 MOI RSV infection for 36 hours) revealed enhanced apoptosis of PC-3 cells by RSV compared to RWPE-1 cells (FIG. 2B). The oncolytic effect of was shown to be specific to RSV, since a different paramyxovirus, human parainfluenza virus-3, failed to replicate efficiently in PC-3 cells and did not promote cell death in PC-3 cells. Viability of cancer cells was not affected by UV-inactivated RSV demonstrating that replicating RSV is needed for the oncolytic activity. The enhanced viral burden in PC-3 cells thus led to selective destruction of the cancer cells in vitro due to apoptosis.

Example 3

RSV-Mediated Oncolysis of PC-3 Cells In Vivo in Xenograft Tumors

Figure 3:
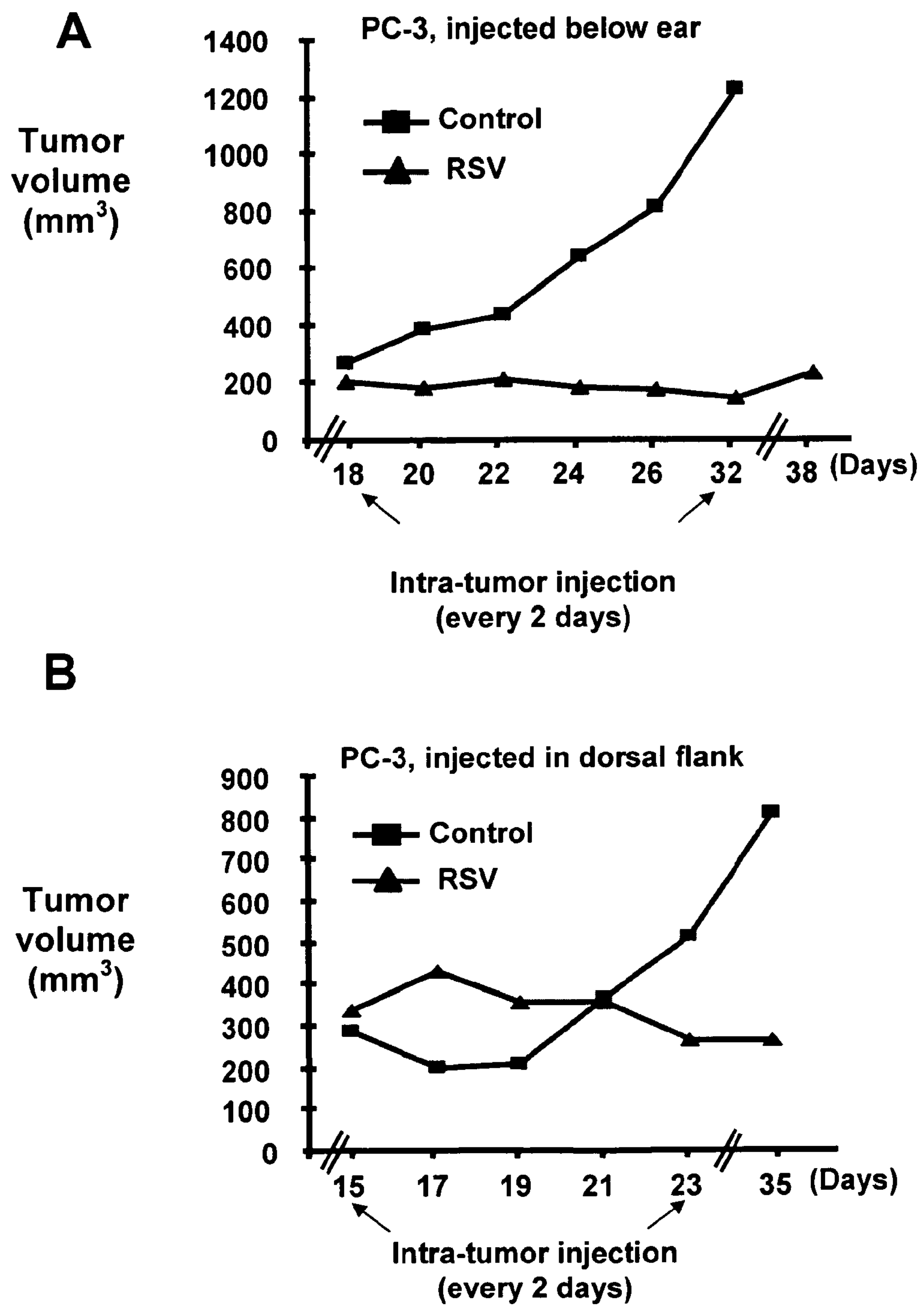

This example illustrates that RSV can exert selective anti-cancer activity against tumors in vivo by showing the in vivo oncolytic effect of injected RSV on prostate tumor xenograft. Seven weeks old athymic male nude mice (Jackson Laboratory, Bar Harbor, Me.) were subcutaneously injected with infected PC-3 cells ($3\text{-}5\times10^6$ cells in 1000) as prepared above at either a site slightly below the ear or in the dorsal flank. When the tumor size reached 200 $mm^3$, RSV ($1\times10^6$ pfu per animal) or Opti-MEM medium (control) was injected intratumorally. At 2-day intervals, RSV was injected for the next 8 days and the tumors were measured until 35 days to 38 days post-infection. Tumor volumes were measured up to 35 days to 38 days post-infection (FIGS. 3A and B).

Intra-tumoral RSV injection led to a drastic reduction in tumor mass below the ear and at the flank. In contrast, the size of the non-infected tumors (control) steadily increased. The ability of RSV to mediate tumor regression further demonstrated in an in vivo setting that RSV is an oncolytic virus. Moreover, RSV mediated restriction of tumor growth at two sites (ear and flank) demonstrated the versatility of RSV in conferring oncolysis in vivo at different anatomical regions.

Figure 4:
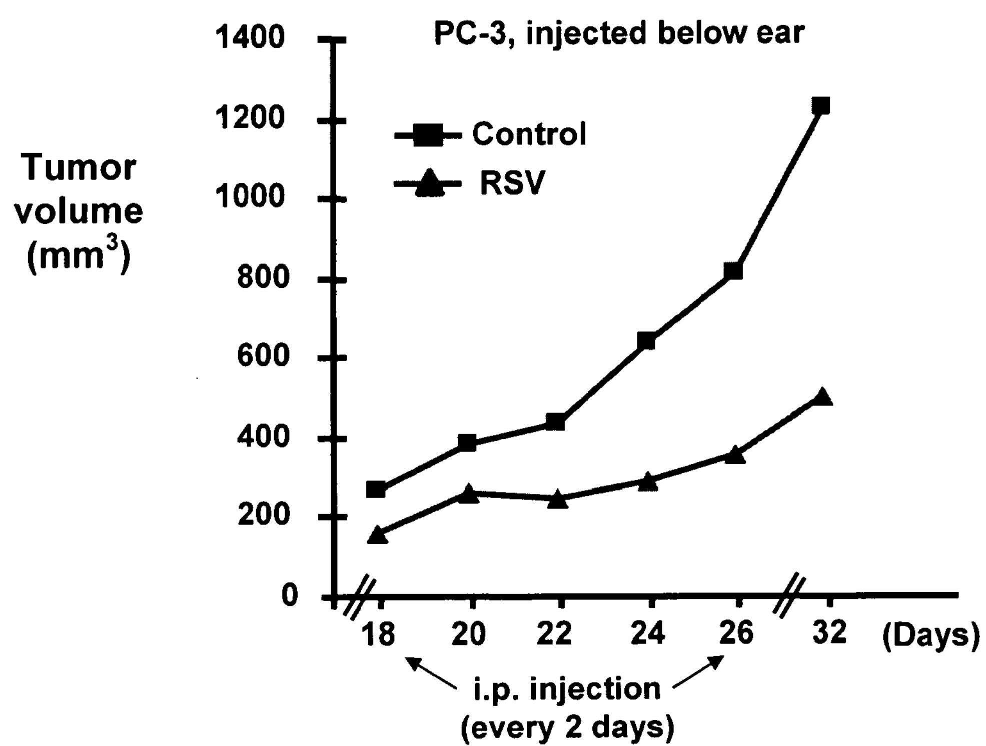

The ability of RSV to induce tumor regression was also measured following intra-peritoneal injection. Systemic injection ensures ease of delivery and the ability of the virus to access tumors residing in various parts of the body (resulting from metastasis). Tumors from PC-3 cells were produced below the ear as described above and intra-peritoneal injection of RSV ($10^6$ pfu/mouse) was started when the tumor size reached about 200 $mm^3$. The intra-peritoneal injections were administered for 8 days at 2 day intervals. Intra-peritoneally injected RSV was able to restrict tumor growth at the ear site (FIG. 4). Injection of RSV significantly decreased the growth of tumors compared to the control treatment. The significant regression of tumors by RSV could also be observed visually. Intra-peritoneal injection of high doses of RSV ($10^8$ pfu/mouse; eight injections at 2 day intervals) in nude mice (with no tumor burden) did not cause any disease state even after 2 months following RSV injection, thus demonstrating the inability of RSV to establish productive systemic infection. RSV was also not detectable in the systemic circulation at 2 days post intra-peritoneal injection. This suggests that RSV could not systemically infect normal cells (by virtue of being a respiratory virus that infects the airway lumen) to establish productive infection. However, the virus nonetheless did become concentrated in the tumor micro-environment, allowing it to infect and kill cancer cells, thus inhibiting tumor growth.

Example 4

Tumor-Specific Targeting of RSV

This example illustrates tumor-specific targeting of RSV. RSV was genetically engineered to express green fluorescent protein (GFP). The resulting recombinant RSV, named GFP-RSV, was then used to study viral targeting and localization upon injection into tumor bearing mice. Mice bearing prostate tumors near the ear were either injected with medium (control) or GFP-RSV via intra-tumoral or intra-peritoneal injection.

Following virus administration, the fluorescence emitted from the viral GFP was measured in live animals using a real-time optical imaging scanner. The fluorescence density was depicted by a color intensity bar. Red color represented the highest amount of fluorescence, while purple/blue was considered background. Green, yellow, and red colors were considered high, higher and highest.

In control mice, the background blue fluorescence was clearly visible when the animals were placed under excitation light. In contrast, RSV-GFP administration led to intensification of fluorescence density in close proximity of the tumor. Both intra-tumoral and intra-peritoneal injection resulted in localized fluorescence near the tumor. Very high intensified GFP expression (yellow and red color) was clearly visible when the animals were photographed under high excitation light. This demonstrates tumor-specific localization of RSV and failure of RSV to cause systemic infection in non-tumorogenic normal organs and tissues. These data provide evidence for the inability of RSV to establish systemic infection and the high specificity of RSV for tumors.

The foregoing detailed description demonstrates the potential usefulness of RSV as a locally or systemically delivered oncolytic virus for cancer treatment. The RSV-mediated oncolysis of PC-3 cells in vitro in culture and in vivo in xenograft tumors demonstrates the potent, novel oncolytic function of RSV that can be used to develop an efficacious virotherapy strategy for cancer.

Example 5

Further Studies on Oncolytic Mechanism of RSV

Virus and Cells.

RSV (A2 strain) was propagated in CV-1 cells. RWPE and PC-3 cells were from ATCC. The viral titer was monitored by plaque assay analysis (1, 2, 3).

RSV Infection of RWPE and PC-3 Cells.

RSV (0.2 or 2 MOI) was added to cells for adsorption at 37° C. for 1.5 h and following washing, infection was continued for an additional 4 h-42 h. At various post-infection time periods, the culture supernatants were collected to measure virus yield by plaque assay analysis. For some infected cells, the cell morphology was visualized microscopically.

Apoptosis and Cell Viability Assay.

Cells infected with RSV for 36 h were used to examine apoptosis and cell viability. Cell cytotoxicity of infected cells was quantified by determining the number of viable cells using a MTT assay (4). For apoptotic analysis, dissociated cells were fixed with cold ethanol and used for TUNEL analysis (5) (Roche, Germany). DNA in apoptotic nuclei incorporated fluorescein-labeled nucleotides and was analyzed by fluorescence activated cell sorting (FACS). Apoptosis was also performed using the annexin V/propidium iodide apoptosis detection kit (BioVision). In order to visualize apoptosis in tumors, single cell suspensions prepared from surgically excised tumors (6) were used to detect annexin V.

Caspase Inhibitors, Neutralizing Antibodies and NF-κB Inhibitory SN50 Peptide.

PC-3 cells were pre-treated with control inhibitor (Z-FA-FMK) or caspase-3 (Z-DQMD-FMK), -8 (Z-IETD-FMK), -9 (Z-LEHD-FMK), -3/7 (Z-DEVD-FMK) (Calbiochem) and -12 (Z-ATAD-FMK) (MBL) inhibitors for 1 h at 37° C. Caspase-3, -8, -9 and -3/7 inhibitors at 15 μM-60 μM were used, while the caspase-12 inhibitor was used at 50 μM-100 μM. RSV was added to cells for adsorption at 37° C. for 1.5 h. The cells were then washed and the infection was continued for an additional 36 h in the presence of inhibitors, following which apoptosis analysis was performed by TUNEL assay. For neutralizing studies, PC-3 cells were infected with RSV in the presence of 900 ng/ml of interleukin-1β (IL-1) or TNF-neutralizing antibodies (R&D Systems). In some experiments, infection was performed in the presence of both neutralizing antibody and caspase-3 or -8 inhibitors. At 36 h post-infection, cells were assayed for apoptosis. PC-3 and RWPE cells were pre-treated with either SN50 peptide (30 μM) or control SN50M (50 μM) peptide (Calbiochem) for 2 h, followed by virus infection (in the presence of peptides) for 0 h-36 h, after which cells were analyzed for apoptosis.

Reverse Transcription-PCR (RT-PCR).

Total cellular RNAs isolated from PC-3 cells/tumors infected with RSV were used to generate cDNAs for RT-PCR analysis to detect human and mouse TNF and GAPDH (for loading control) (7, 8).

Western Blot and EMSA.

Mock infected or RSV infected PC-3 cell lysates (50 μg protein) or tumor homogenate (100 μg protein) was subjected to either 7.5% or 15% SDS-PAGE and Western blot analysis as described previously (1, 2). Bcl-2, Bcl-xL, Bad, Bax antibodies were obtained from Cell Signaling, while caspase-3, PARP and GFP antibodies were from Santa Cruz. Heat shock protein-70 (Hsp70) (Santa Cruz) antibody was used as a loading control. Nuclear extracts prepared from infected cells were incubated with a $^{32}$P-labeled NF-κB oligonucleotide probe and analyzed for EMSA as described previously.

Prostate Cancer Xenograft Tumors in Nude Mice.

Seven weeks old athymic nude mice (Jackson Laboratory) were subcutaneously injected with PC-3 cells (3-5×$10^6$ cells in 100 μl) at a site slightly below the ear (9). When the tumor size reached 200 mm$^3$, RSV (1×$10^6$ pfu per animal) or Opti-MEM (carrier control) was injected either intra-tumorally (I.T) or via intra-peritoneal (I.P) route. At 2-day intervals, RSV was injected for the next 8-14 days and the tumors were measured until 35d-38d post-infection. In some experiments, tumor bearing mice were injected (I.T or I.P) with GFP-RSV. At 16 h post-infection, the animals were euthanized and the tumor was surgically excised. The tumor was then homogenized with Trizol or PBS for extraction of RNA and protein, respectively.

The Oncolytic Activity of RSV Against PC-3 Human Prostate Cancer Cells.

Selective enhancement of RSV infectivity (at 36 h post-infection) in PC-3 cells as compared with RWPE-1 (RWPE) non-malignant prostate cells was observed. RSV infection was dramatically augmented (by 10,000 fold) in the PC-3 cancer cells compared to the non-tumorigenic RWPE cells. Thus, in RWPE cells, the viral titer is 1000 pfu/ml, while in PC-3 cells the titer is 1×$10^7$ pfu/ml. A single step virus growth curve also revealed much more robust growth of RSV in PC-3 cells compared to RWPE cells. An MTT cell viability assay performed with infected PC-3 and RWPE cells demonstrated loss of viable PC-3 (but not RWPE cells) cells due to high viral burden in these cells. The much greater cytopathic effect and loss of cell viability of RSV infected PC-3 cells compared to RWPE cells is shown by the significantly higher cell death, evident from cell rounding and loss of normal cellular morphology. The oncolytic effect of RSV is specific, since human parainfluenza virus-3 (a RSV related paramyxovirus) (1, 2) failed to replicate efficiently in PC-3 cells and did not promote loss of cell viability. The 10,000-fold enhancement of viral infectivity and associated robust RSV growth in vitro in cancer cells compared to normal cells strongly implicated RSV as an oncolytic virus.

The Oncolytic Effect of RSV In Vivo on Human Prostate Tumor Xenografts.

The efficacy of the oncolytic function of RSV was tested in a human prostate tumor xenograft model. Intra-tumoral (I.T) RSV injection of PC-3 tumors below the ear led to a drastic reduction in tumor mass. In contrast, the size of the non-infected tumors (carrier control) steadily increased.

Systemic injection of oncolytic virus is a preferred route of delivery, since it ensures ease of delivery and the ability of virus to access tumors residing in various parts of the body (resulting from metastasis). Thus, the ability of RSV to induce tumor regression following its intra-peritoneal (I.P) injection was investigated. Injection (I.P) of RSV significantly decreased the growth of tumors compared to the control, medium treatment. The ability of RSV to mediate tumor regression further established RSV as an oncolytic virus in an in vivo setting. RSV was also observed to mediate regression of PC-3 tumors grown in the dorsal flank of nude mice. Thus, RSV mediated restriction of tumor growth at two sites (ear and flank) demonstrated the versatility of RSV in conferring oncolysis in vivo at different anatomical regions.

Notably, I.P injection of high doses of RSV ($10^8$ pfu/mouse; eight injections at 2d intervals) in nude mice (with no tumor burden), did not cause any disease state even after two months following RSV injection, thus demonstrating the inability of RSV to establish productive systemic infection. In addition, RSV was not detected in the systemic circulation at 2d post I.P injection. These results suggest that RSV cannot systemically infect normal cells (by virtue of being a respiratory virus that specifically infects the airway lumen) to establish productive infection. However, the virus gets concentrated in the tumor micro-environment to infect and kill cancer cells, thus inhibiting tumor growth. These results demonstrate a potent oncolytic function of RSV in vivo and show the utility of RSV as a systemically delivered oncolytic virus for prostate cancer treatment.

To demonstrate tumor-specific targeting/localization of systemically administered RSV, green fluorescent protein (GFP) expressing RSV (GFP-RSV) (10) was utilized. This recombinant virus harbors the GFP cDNA fused to the viral genome, thus expression of GFP can only occur following infection. Mice bearing prostate tumors near the ear were either injected with medium (control mock infection) or GFP-RSV via I.T or I.P injection. In order to demonstrate presence of RSV-GFP in tumors, the tumors were surgically excised from the euthanized mice. Western blot analysis of tumor homogenate with anti-GFP antibody revealed the expression of GFP in tumors of infected mice. These results clearly demonstrate localization of RSV in the tumor.

The Role of Mitochondria-Dependent Intrinsic Pathway in RSV Induced Apoptosis of Prostate Cancer Cells.

The loss of cell viability of infected PC-3 cells was due to apoptosis; since TUNEL assay with RSV infected cells revealed enhanced apoptosis of PC-3 cells by RSV compared to RWPE cells. In addition to TUNEL assay, which detects late apoptotic events, annexin V staining (signifying early apoptosis) also confirmed the ability of RSV to induce apoptosis in PC-3 cells. Annexin V staining revealed that 0.2% and 52% of cells undergoing early apoptosis (cells in the lower right quadrant) following RSV infection of RWPE and PC-3 cells, respectively.

Caspase-3 plays a central role in apoptosis. Since RSV induced apoptosis in PC-3 cells, studies were carried out to investigate whether virus infection results in activation of caspase-3. PC-3 cells infected with RSV for 8 h and 16 h were subjected to Western blot analysis with anti-caspase-3 antibody that can recognize the full-length pro-caspase-3. While mature full-length pro-caspase-3 was detected in mock infected cells, RSV infection resulted in the loss of pro-caspase-3, thus demonstrating the ability of RSV to cleave activate caspase-3 in PC-3 cells.

PARP is a substrate for activated caspase-3 and cleaved PARP is considered a hallmark of apoptosis (11). Western blot analysis of RSV infected PC-3 cells with anti-PARP antibody (that can detect the full-length PARP) revealed cleavage of PARP in virus infected cells, since full-length PARP could not be detected in infected cells. PARP cleavage can be mediated by either caspase-3 or caspase-7 or both. However, RSV induced PARP cleavage was caspase-3 dependent, since treatment of infected cells with cell permeable, irreversible caspase-3 inhibitor (Z-DQMD-FMK) prevented PARP cleavage. In addition, caspase-3/7 inhibitor (Z-DEVD-FMK) also prevented PARP cleavage in infected cells. These results suggested that PARP cleavage is primarily mediated by caspase-3 and not by caspase-7.

Caspase-3 activation via the intrinsic apoptotic pathway is regulated by proteins belonging to the Bcl-2 family. Bcl-2 family proteins include a number of pro-apoptotic (e.g., Bax and Bad) and anti-apoptotic (e.g., Bcl-2 and Bcl-xL) proteins that regulate mitochondria-mediated apoptosis. In order to investigate whether intrinsic pathway apoptosis is the major pathway for caspase-3 activation, the expression of pro-apoptotic and anti-apoptotic proteins was investigated in RSV infected PC-3 cells. Western blot analysis of cell lysates with Bad, Bax, Bcl-2 and Bcl-xL antibodies revealed a gradual decrease in anti-apoptotic protein (Bcl-2 and Bcl-xL) expression following RSV infection. In contrast, the expression of pro-apoptotic proteins (Bad and Bax) increased steadily in virus infected cells. The pre-dominance of the pro-apoptotic signal over anti-apoptotic signal indicates the important role of mitochondria-mediated apoptosis (intrinsic pathway) in caspase-3 activation following RSV infection.

The Role of the Death-Receptor-Mediated (Extrinsic Pathway) and Caspase-12-Mediated (ER-Stress Pathway) Pathways in RSV-Induced Apoptosis.

The extrinsic pathway to apoptosis is induced following engagement of death receptors (e.g., TNF-receptor and Fas) with cognate ligands (TNF and FasL), leading to the activation of caspase-8. The ER-stress pathway (12) activation leads to activation of caspase-12. Activation of both caspase-8 and caspase-12 results in caspase-3 activation and apoptosis. In order to explore the contribution of non-intrinsic pathway in apoptosis induction by RSV, infection experiments were conducted in the presence of various cell permeable, irreversible caspase inhibitors. PC-3 cells treated with control and caspase-3, -9, -8, and -12 inhibitors, respectively, were infected with RSV and at 36 h post-infection, cellular apoptosis was evaluated by TUNEL assay. As expected, inhibition of caspase-3 resulted in drastic decline (by 85%) in apoptosis. Similarly, blocking caspase-9 activity also led to significant inhibition (by 75%) in apoptosis. These results confirm data showing activation of intrinsic pathway (involving activation of caspase-9 and caspase-3) as the major apoptotic pathway induced by RSV. In contrast to caspase-3 and -9, inhibition of caspase-12 did not alter apoptosis in virus infected cells. The caspase-12 inhibitor was active since it inhibited RSV mediated apoptosis significantly (by 40%) in human lung epithelial A549 cells, the cells in which the involvement of caspase-12 was demonstrated previously (13). It was interesting to note that inhibition of caspase-8 resulted in decrease in apoptosis by 15%. This result suggested that extrinsic pathway may play a minor role in RSV mediated apoptosis. It is important to note that the caspase-8 inhibitor is active, since it reduced interferon-γ+Fas antibody mediated apoptosis (14) in A549 cells by 60%. During the caspase inhibitor studies, 15 μM inhibitor concentration was optimal for inhibiting apoptosis mediated by caspase-3, -9 and -8, since higher concentration (20 μM-60 μM) did not augment apoptotic inhibitory activity. Similarly, a high concentration (up to 100 μM) of caspase-12 failed to inhibit apoptosis in infected PC-3 cells. Treatment of cells with the caspase inhibitors did not affect cell viability during the time frame of this experiment.

Studies were carried out to determine whether caspase-8 dependent apoptosis may be mediated by the autocrine/paracrine action of TNF produced from infected PC-3 cells, which would bind to the TNF-receptor to activate caspase-8. Infection of PC-3 cells led to expression of TNF as early as 8 h post-infection as detected by RT-PCR analysis. Similarly, TNF protein was detected in the culture supernatant of infected PC-3 cells, as assessed by TNF specific ELISA analysis. The contribution of secreted TNF in activation of the extrinsic apoptotic pathway was examined by utilizing neutralizing antibody against TNF. PC-3 cells incubated with neutralizing antibodies to either interleukin-1β (IL-1) (control) or TNF were infected with RSV. The apoptosis assay revealed that while IL-1 antibody had no effect, presence of TNF neutralizing antibody decreased apoptosis by 15%, the same extent of decline that was observed upon caspase-8 inhibition. Further inhibition in apoptosis was not observed in cells treated with both TNF neutralizing antibody and caspase-8 inhibitor. This result demonstrated that the minor extrinsic pathway involving caspase-8 activation is exclusively activated via the paracrine/autocrine action of TNF produced from infected cells. Furthermore, it was demonstrated that extrinsic pathway is playing a minor role (as opposed to the intrinsic pathway) in apoptosis, since a dramatic decline in apoptosis was observed in cells incubated with both TNF neutralizing antibody and caspase-3 inhibitor. This dramatic decline was due to the inability of activated caspase-9 (activated by the intrinsic pathway) to activate caspase-3 for apoptosis.

RSV-Induced Apoptosis In Vivo in Prostate Tumors.

In order to examine the physiological relevance of apoptosis during oncolytic activity of RSV, apoptosis was studied in tumors isolated from mice injected with RSV. Mice bearing prostate tumors near the ear were injected with RSV via the I.T or I.P route as described above. At 16 h post-infection, the mice were euthanized and the tumors were surgically removed. Cell suspension prepared from the tumors was used for the apoptosis assay. Apoptosis assay with annexin V staining revealed 5%-7.5% apoptotic cells in control tumors (mice injected with control medium), while 35%-42% and 22%-26% of tumor cells were apoptotic following I.T or I.P injection of RSV, respectively. These studies also show that both intrinsic and extrinsic pathways are operative during apoptosis of infected tumors. Activation of intrinsic pathway is evident from expression of pro-apoptotic Bax protein in virus infected (I.T) tumor. In contrast, anti-apoptotic Bcl-xL protein expression was suppressed following I.T infection. Similarly, extrinsic pathway may also be induced, since TNF expression was induced in tumors following RSV infection (I.T), which based on in vitro results, will act via a paracrine/autocrine mechanism to activate the extrinsic pathway. Similar results were obtained following RSV injection via the I.P route. These results show that the tumors undergo apoptosis following RSV infection, which then contributes to oncolysis and the associated regression of tumor volume.

The Role of NF-κB in the Apoptosis of RSV-Infected Prostate Cells.

The contribution of Akt and NF-κB activity to RSV mediated apoptosis of prostate cancer cells was also investigated. EMSA revealed activation (as early as 1 h post-infection) of NF-κB in RSV infected RWPE cells. By contrast, there was only marginal activation of NF-κB over the basal NF-κB activity in RSV-infected PC-3 cells at 1 h. By 6 h post-infection, NF-κB activity in PC-3 cells was markedly diminished, whereas NF-κB activity was sustained in infected RWPE cells at 6 h and 10 h post-infection. The NF-κB-specific cell-permeable inhibitory peptide SN50 (blocks nuclear translocation of NF-κB) (16, 17) induced apoptosis of infected RWPE cells. Similarly, SN50 treatment resulted in significantly enhanced apoptosis of PC-3 cells during early infection time periods (12 h post-infection). The effect of SN50 was specific, since control SN50M peptide had no effect on apoptosis. Similar results were obtained in the presence of another NF-κB inhibitor PDTC. These results indicate that the anti-apoptotic function of NF-κB determines the apoptotic fate of infected prostate cells. Infected RWPE cells do not undergo apoptosis due to failure of RSV to block NF-κB activity; while the ability of RSV to down-regulate NF-κB activity in PC-3 cells results in apoptosis and oncolysis following infection. In contrast to NF-κB, inhibition of Akt activity had no effect on the apoptosis status in RSV infected PC-3 and RWPE cells. These studies indicate that NF-κB induction plays a key role in anti-apoptotic function of infected RWPE cells, while its inhibition by RSV in PC-3 cells commits cells to virus mediated apoptosis and oncolysis.

These studies have demonstrated the oncolytic function of RSV. In prostate cancer model systems (in vitro and in vivo using tumor xenografts), RSV infection rate was shown to be dramatically enhanced in cancer cells, but not in normal cells. As a result of such increased viral burden, the infected cancer cells undergo loss of cell viability. Validation of the in vitro results came from using prostate tumor xenografts in nude mice, which showed significant tumor regression in response to intra-tumoral or I.P administration of RSV. These results clearly show a potent oncolytic property of RSV. RSV mediated oncolysis has been shown to be due to apoptosis that was induced primarily by the mitochondria-mediated activation of intrinsic pathway involving caspase-3 activation, and that resulted from impaired NF-κB activity.

RSV is especially advantageous as an oncolytic virus for the following reasons. 1) RSV confers mild respiratory illness in infants and children, while infection is asymptomatic in adults. 2) RSV does not establish systemic infection, since it is a respiratory virus infecting lung epithelial cells via the apical domain of airway lumen. Thus, so far the presence of RSV in the serum has not been detected in infected individuals. This property is highly desirable for cancer treatment because systemic delivery of RSV will only destroy tumor cells while keeping the normal cells intact, resulting in limited toxicity to normal tissues. 3) RSV replication occurs in the cytoplasm of infected cells (4) and therefore RSV does not possess transforming potential due to genetic recombination. 4) Immune response against RSV is not robust, which accounts for non-symptomatic re-infection throughout life (4). 5) The RSV genetic makeup of only ten genes facilitates its manipulation by reverse genetics. This technology may be used to produce "efficient and safe" recombinant attenuated RSV-based vectors for anti-cancer therapy. 6) Systemic delivery of RSV is efficacious for targeting tumor-specific killing, since I.P injection of RSV resulted in the regression of prostate tumors in mice. In addition, the virus was specifically targeted to the tumor to confer its oncolytic activity.

Most advanced stage cancer cells including androgen-independent prostate cancer cells (like PC-3) are resistant to apoptosis. Thus, a major challenge is to develop therapeutic agents that would induce apoptosis in these cells leading to tumor regression. Results presented herein have revealed that RSV confers its anti-tumor oncolytic activity in prostate cancer PC-3 cells by inducing apoptosis. RSV mediated apoptosis in prostate cancer PC-3 cells occur via both the death-receptor-mediated extrinsic pathway and mitochondria-mediated intrinsic pathway; although the later pathway is the major one. RSV infection results in the suppression of NF-κB activity, leading to up-regulation and down-regulation of pro-apoptotic and anti-apoptotic proteins, respectively. In addition, caspase-3 and its substrate PARP cleavage occurs during infection. Studies with caspase specific inhibitors also confirmed these observations, since apoptosis was significantly reduced in the presence of caspase-3 and -9 inhibitors. Although the intrinsic pathway constitutes the major apoptotic mechanism in infected cells, the extrinsic pathway also plays a minor role in apoptotic induction; particularly via activation of caspase-8 by TNF secreted from the infected cells. These results show that caspase-8 inhibitor reduced apoptosis by 15%. These results further demonstrate that RSV stimulates TNF production from infected cells and neutralization of TNF activity results in inhibition of apoptosis by 12-15%. Thus, the extrinsic pathway plays a minor role in apoptotic induction and autocrine/paracrine action of TNF produced from infected cells activates the extrinsic pathway in both infected and un-infected cells (by-stander cells). Moreover, TNF is the sole inducer of the extrinsic pathway, since the degree of inhibition of apoptosis was similar in cells treated with either TNF neutralizing antibody or caspase-8 inhibitor. Similar inhibitory effect was observed in cells incubated with both TNF neutralizing antibody and caspase-8 inhibitor.

REFERENCES FOR EXAMPLE 5

1. Bose S, Basu M, Banerjee A K. Role of nucleolin in human parainfluenza virus type 3 infection of human lung epithelial cells. J Virol 2004; 78: 8146-58.
2. Bose S, Kar N, Maitra R, DiDonato J A, Banerjee A K. Temporal activation of NF-κB regulates an interferon-independent innate antiviral response against cytoplasmic RNA viruses. Proc Natl Acad Sci USA 2003; 100:10890-95.
3. Bose S, Malur A, Banerjee A K. Polarity of human parainfluenza virus type 3 infection in polarized human lung epithelial A549 cells: role of microfilament and microtubule. J Virol 2001; 75:1984-89.
4. Pauwels R, Balzarini J, Baba M, et al. Rapid and automated tetrazolium-based colorimetric assay for the detection of anti-HIV compounds. J Virol Methods 1988; 20: 309-21.
5. Hara F, Aoe M, Doihara H, et al. Antitumor effect of gefitinib ('Iressa') on esophageal squamous cell carcinoma cell lines in vitro and in vivo. Cancer Lett 2005; 226: 37-47.
6. Muruganandham M, Alfieri A A, Matei C, Chen Y, Sukenick G, Schemainda I, Hasmann M, Saltz L B, Koutcher J A. Metabolic signatures associated with a NAD synthesis inhibitor-induced tumor apoptosis identified by 1H-decoupled-31P magnetic resonance spectroscopy. Clin Cancer Res 2005; 11:3503-13.
7. Kang J S, Yoon Y D, Han M H, Han S B, Lee K, Kang M R, Moon E Y, Jeon Y J, Park S K, Kim H M. Estrogen receptor-independent inhibition of tumor necrosis factor-alpha gene expression by phytoestrogen equol is mediated by blocking nuclear factor-kappaB activation in mouse macrophages. Biochem Pharmacol 2005; 71:136-43.
8. Frigo D E, Vigh K A, Struckhoff A P, Elliott S, Beckman B S, Burow M E, McLachlan J A. Xenobiotic-induced TNF-alpha expression and apoptosis through the p38 MAPK signaling pathway. Toxicol Lett. 2005; 155:227-38.
9. Jounaidi Y, Waxman D J. Use of replication-conditional adenovirus as a helper system to enhance delivery of P450 prodrug-activation genes for cancer therapy. Cancer Res 2004; 64:292-303.
10. Hallak L K, Collins P L, Knudson W, Peeples M E. Iduronic acid-containing glycosaminoglycans on target cells are required for efficient respiratory syncytial virus infection. Virology 2000; 271:264-75.
11. Soldani C, Scovassi A I. Poly(ADP-ribose) polymerase-1 cleavage during apoptosis: an update. Apoptosis 2002; 7:321-28.
12. Szegezdi E, Fitzgerald U, Samali A. Caspase-12 and ER-stress-mediated apoptosis: the story so far. Ann N Y Acad Sci 2003; 1010:186-94.
13. Bitko V, Barik S. An endoplasmic reticulum-specific stress-activated caspase (caspase-12) is implicated in the apoptosis of A549 epithelial cells by respiratory syncytial virus. J Cell Biochem 2001; 80:441-54.
14. Kim K B, Choi Y H, Kim I K, Chung C W, Kim B J, Park Y M, Jung Y K. Potentiation of Fas- and TRAIL-mediated apoptosis by IFN-gamma in A549 lung epithelial cells: enhancement of caspase-8 expression through IFN-response element. Cytokine 2002; 20:283-88.
15. Jiang Z, Kunimoto M, Patel J A. Autocrine regulation and experimental modulation of interleukin-6 expression by human pulmonary epithelial cells infected with respiratory syncytial virus. J Virol 1998; 72:2496-99.
16. Orlandi A, Francesconi A, Marcellini M, Di Lascio A, Spagnoli L G. Propionyl-L-carnitine reduces proliferation and potentiates Bax-related apoptosis of aortic intimal smooth muscle cells by modulating nuclear factor-kappaB activity. J Biol Chem 2007; 282:4932-42.
17. Naderi A, Teschendorff A E, Beigel J, Cariati M, Ellis I O, Brenton J D, Caldas C. BEX2 Is overexpressed in a Subset of Primary Breast Cancers and Mediates Nerve Growth Factor/Nuclear Factor-κB Inhibition of Apoptosis in Breast Cancer Cell Lines.
Cancer Res 2007; 67: 6725-36.

Example 6

Oncolysis of Primary Prostate Tumor Cells Using a Nano-Particle Based Delivery Strategy Nanoparticles coated with various molecules (DNA, protein, RNA) are extensively utilized to deliver molecules to specific tissues/cells (1). A similar strategy is employed to develop a "safe and efficient" RSV that could specifically infect (and promote cell death) prostate cancer cells, while leaving normal cells intact. Development of an RSV based therapeutic agent is carried out using reverse genetics technology to produce recombinant RSV (2).

The production of nanoparticle-based safe RSV will involve generation of RSV that lacks glycoprotein (G). RSV lacking G protein can enter cells efficiently, but fails to establish productive infection, particularly in vivo (in a mouse model of RSV infection), since G is a key protein required for pathogenesis (3, 4). RSV lacking G protein (RSVΔG) will be produced and used as a tool for generating safe virus that specifically infects and propagates in prostate tumors. This will be achieved by converting RSVΔG into an infectious/pathogenic virus upon prostate tumor cell-specific expression of G protein.

The tumor cell-specific G protein expression strategy is developed by utilizing nanoparticles containing G protein cDNA under the control of a prostate tumor cell specific promoter (g., probasin promoter for mice) RSVΔG virion particles will be coated with these nanoparticles to create RSV-nano. RSV-nano will fail to infect normal tissues/cells since they lack prostate tumor cell specific promoters and as a result G protein will not be expressed in these normal cells. In contrast, G protein will be expressed in prostate tumors due to the presence of prostate tumor cell specific promoter elements in the G cDNA. Expression of G protein will result in RSV growth/replication in tumor cells, leading to apoptosis and oncolysis.

The oncolytic activity of RSVΔG virus will be first examined using RWPE-1 and PC-3 cells in culture. These cells will be infected with RSVΔG virus and at various time post infection, virus titer, cell viability and apoptosis rate will be measured. Wild-type RSV will be used as a control. In addition, the in vivo efficacy of RSVΔG virus will be studied by using PC3 xenograft mice.

RSV G cDNA, will be cloned into a pCAAG vector containing $ARR_2PB$ sequences (15) (minimal probasin promoter) (pCAAG-PB/G plasmid). A control plasmid (pCAAG-PB/mut-G plasmid) expressing mutant G protein (a deleted G protein that cannot be incorporated into the virus particle, therefore the virus is non-infectious) will also be generated. The efficiency of prostate cancer cell specific expression of G protein will be tested by transfecting pCAAG-PB/G in RWPE-1, PC-3, mouse RM1 (mouse prostate cancer cells) and 3T3 mouse fibroblast cells. Expression of G protein will be monitored by Western blot analysis with anti-G antibody. G protein should be expressed only in RM1 cells, but not in other cells since probasin is a mouse prostate cancer cell specific promoter. Nanoparticles (cationic poly-b-amino ester polymer/C32) will be synthesized by utilizing standard protocols established previously (6). The pCAAG-PB/G or pCAAG-PB/mut-G DNA will be complexed to C32 as described (6). In some embodiments, magnet-based nanoparticles (ViroMag), which are commercially available from OZbiosciences can be used to coat RSV.

In order to coat RSVΔG with the nanoparticles, C32 particles (conjugated to pCAAG-PB/G or pCAAG-PB/mut-G DNA) will be incubated with RSVΔG at various conditions as described (6). The resulting RSV-nano (containing pCAAG-PB/G) or RSV-mut-nano (containing pCAAG-PB/mut-G) will be used to infect RWPE-1, PC-3, mouse RM1 and 3T3 mouse fibroblast cells. Expression of G protein will be measured by Western blot analysis. Oncolytic activity will be deduced by measuring viral titer, cell viability and apoptosis rate. It is expected that G protein will be expressed only in RM1 cells and RSV-nano will specifically induce apoptosis in RM1 cells. In contrast, RSV-mut-nano will not possess oncolytic activity.

A prostate tumor xenograft in mice will be developed using RM1 cells to examine the oncolytic potential of RSV-nano. RSV-nano and RSV-mut-nano (control) will be administered either IT or IP and the effect of the virus on tumor progression will be studied as described above for human derived xenografts. RSV-nano is expected act as an oncolytic virus by halting tumor progression.

RSV expressing G protein under the control of human prostate cell specific promoters (e.g., PSA promoter) will also be developed. These recombinant viruses will be utilized to study oncolytic activity in xenografts developed using human primary tumor cells (LAPC-3, LAPC-4, and LAPC-9 cells) and orthotopic tumor xenografts as described above.

REFERENCES FOR EXAMPLE 6

1) Pridgen E M, Langer R, Farokhzad O C. Biodegradable, polymeric nanoparticle delivery systems for cancer therapy. Nanomed. 2007. 2:669-80.
2) Murphy B R, Collins P L. Live-attenuated virus vaccines for respiratory syncytial and parainfluenza viruses: applications of reverse genetics. J Clin Invest. 2002. 110:21-27.
3) Techaarpornkul S, Barretto N, Peeples M E. Functional analysis of recombinant respiratory syncytial virus deletion mutants lacking the small hydrophobic and/or attachment glycoprotein gene. J. Virol. 2001.75:6825-34.
4) Teng M N, Whitehead S S, Collins P L. Contribution of the respiratory syncytial virus G glycoprotein and its secreted and membrane-bound forms to virus replication in vitro and in vivo. Virology. 2001.289:283-96.
5) Johnson M A, Hernandez I, Wei Y, Greenberg N. Isolation and characterization of mouse probasin: An androgen-regulated protein specifically expressed in the differentiated prostate. Prostate. 2000. 43:255-62.
6) Peng W, Anderson D G, Bao Y, Padera R F Jr, Langer R, Sawicki J A. Nanoparticulate delivery of suicide DNA to murine prostate and prostate tumors. Prostate. 2007. 67:855-62.

Although the compositions and methods of this invention have been described in terms of specific embodiments and illustrative examples, it will be apparent to those of skill in the art that variations can be applied to the compositions and methods described herein without departing from the concept, spirit and scope of the invention. All such similar substitutes and modifications apparent to those skilled in the art are deemed to be within the spirit, scope and concept of the invention as defined by the appended claims.

Throughout this application, various, patents, patent publications and non-patent publications are referenced. The disclosures of these publications in their entireties are incorporated by reference into this application in order to more fully describe the state of the art to which this invention pertains.

What is claimed is:

1. A method of treating a prostate neoplasm in a subject, comprising administering to the subject an oncolytically effective amount of a respiratory syncytial virus (RSV), wherein the RSV does not comprise a heterologous nucleotide sequence, thereby treating the prostate neoplasm in the subject.

2. A method of treating a prostate cancer in a subject, comprising administering to the subject an oncolytically effective amount of a respiratory syncytial virus (RSV), wherein the RSV does not comprise a heterologous nucleotide sequence, thereby treating the prostate cancer in the subject.

3. A method of reducing metastasis of a primary prostate cancer in a subject, comprising administering to the subject an oncolytically effective amount of a respiratory syncytial virus (RSV), wherein the RSV does not comprise a heterologous nucleotide sequence, thereby reducing metastasis of the primary prostate cancer in the subject.

4. A method of reducing tumor size and/or tumor burden in a subject comprising a prostate tumor, comprising administering to the subject an oncolytically effective amount of a respiratory syncytial virus (RSV), wherein the RSV does not comprise a heterologous nucleotide sequence, thereby reducing tumor size and/or tumor burden in the subject.

5. A method of inducing apoptosis of a prostate neoplastic or tumor cell in a subject, comprising administering to the subject an oncolytically effective amount of a respiratory syncytial virus (RSV), wherein the RSV does not comprise a heterologous nucleotide sequence, thereby inducing apoptosis of the prostate neoplastic or tumor cell in the subject.

6. A method of reducing pain caused by a prostate tumor in a subject, comprising administering to the subject an oncolytically effective amount of a respiratory syncytial virus (RSV), wherein the RSV does not comprise a heterologous nucleotide sequence, thereby reducing pain caused by the prostate tumor in the subject.

7. A method of increasing the sensitivity of a prostate tumor cell to radiation, comprising infecting the prostate tumor cell with a respiratory syncytial virus (RSV), wherein the RSV does not comprise a heterologous nucleotide sequence, thereby increasing the sensitivity of the prostate tumor cell to radiation.

8. A method of increasing the sensitivity of a prostate tumor cell to a chemotherapeutic agent, comprising infecting the prostate tumor cell with a respiratory syncytial virus (RSV), wherein the RSV does not comprise a heterologous nucleotide sequence, thereby increasing the sensitivity of the prostate tumor cell to a chemotherapeutic agent.

9. A method of sensitizing a prostate tumor cell to an immune response against RSV, comprising infecting the prostate tumor cell with a respiratory syncytial virus (RSV), wherein the RSV does not comprise a heterologous nucleotide sequence, whereby the respiratory syncytial virus expresses respiratory syncytial virus antigen on the surface of the prostate tumor cell, thereby sensitizing the prostate tumor cell to an immune response against respiratory syncytial virus.

10. A method of treating a prostate tumor or neoplasm in a subject, comprising removing the prostate tumor or neoplasm from the subject and administering to the subject an oncolytic amount of a respiratory syncytial virus (RSV), wherein the RSV does not comprise a heterologous nucleotide sequence, thereby treating a prostate tumor or neoplasm in the subject.

11. A method of reducing the likelihood of recurrence of a prostate tumor or neoplasm in a subject, comprising removing the prostate tumor or neoplasm from the subject and administering to the subject an oncolytic amount of a respiratory syncytial virus (RSV), wherein the RSV does not comprise a heterologous nucleotide sequence, thereby reducing the likelihood of recurrence of a prostate tumor or neoplasm in the subject.

12. A method of eliminating or reducing the number of neoplastic prostate cells in an ex vivo population of neoplastic prostate cells and normal prostate cells, comprising contacting the population with a respiratory syncytial virus (RSV), wherein the RSV does not comprise a heterologous nucleotide sequence, under conditions whereby the respiratory syncytial virus can infect the prostate cells and kill the neoplastic prostate cells, thereby eliminating or reducing the number of neoplastic prostate cells in the ex vivo population.

13. The method of claim 4, wherein the respiratory syncytial virus (RSV) has a mutation in a gene selected from the group consisting of the NS1, NS2, N, P, M, SH, G, F, M2-1/M2-2, and L genes, and any combination thereof.

14. The method of claim 4, further comprising administering an immunosuppressive agent, a chemotherapeutic agent, an immunostimulatory agent, radiation, or any combination thereof, before, during and/or after administration of the RSV.

15. The method of claim 4, wherein the immunosuppressive agent is selected from the group consisting Azathioprine, Alefacept, Anakinra, Anti-lymphocyte globulin, Anti-thymocyte globulin, Ascomycin, Auranofin, Aurothioglucose, Azathioprine, Basiliximab, CNTO 1275, Ciclosporin (Cyclosporine), Cortisol, Cyclic steroids, Daclizumab, Disodium aurothiomalate, Etanercept, Everolimus, Gliotoxin, Gold salts, Gusperimus, Leflunomide, Mercaptopurine, Methotrexate, Mycophenolic acid, Natalizumab, Penicillamine, Pimecrolimus, Prednisone, Rapamycin, Sirolimus, Sodium aurothiomalate, Sulfasalazine, Tacrolimus, and natural anticancer herbal agents, and any combination thereof.

16. The method of claim 14, wherein the chemotherapeutic agent is selected from the group consisting of Anti-estrogens, Anthracyclins, Azacitidine, Azathioprine, Bleomycin, Busulfan, Carboplatin, Capecitabine, Cisplatin, Chlorambucil, Cyclophosphamide, Cytarabine, Dacarbazine, Daunorubicin, Docetaxel, Doxifluridine, Doxorubicin, Epirubicin, Epothilone, Etoposide, 5-Fluorouracil, Gemcitabine, Hydroxyurea, Idarubicin, Imatinib, Interferons, Mechlorethamine, Melphalan, Mercaptopurine, Methotrexate, Mitomycin C, Mitoxantrone, Oxaliplatin, Paclitaxel, Pemetrexed, Retinoic acid, Taxol, Taxotere, Tamoxifen, Teniposide, Thiotepa, Tioguanine, Valrubicin, Vinblastine, Vincristine, Vindesine, and Vinorelbine, and any combination thereof.

17. The method of claim 14, wherein the immunostimulatory agent is selected from the group consisting of immunostimulatory cytokines, oligodeoxynucleotide (ODN), CpG, cytotoxic/apoptotic/suicides genes and proteins, immunostimulatory genes and proteins, and any combination thereof.

18. The method of claim 14, wherein the radiation is gamma radiation.

19. The method of claim 4, wherein the prostate tumor is a solid prostate tumor.

20. The method of claim 2, wherein the prostate cancer is metastatic prostate cancer.

21. The method of claim 4, wherein the prostate tumor is a primary prostate tumor.

22. The method of claim 4, wherein the prostate tumor is a metastatic prostate tumor.

23. The method of claim 4, wherein the tumor size is in a range from about 2 cm to about 30 cm.

24. The method of claim 4, wherein the RSV is delivered directly to the tumor either at a single site or at multiple sites.

25. The method of claim 4, wherein the RSV is delivered to the subject systemically.

26. The method of claim 4, wherein the RSV is administered continuously over a period of time.

27. The method of claim 4, wherein the RSV is administered at intervals of every hour, every two hours, every three hours, every day, every other day, every three days, every week, and/or every month.

28. The method of claim 4, wherein the dose of RSV is administered in a range from about $1\times10^2$ pfu/ml to about $1\times10^8$ pfu/ml of virus particles.

29. The method of claim 4, wherein the subject is selected from the group consisting of humans, nonhuman primates, dogs, cats, horses, cattle, and livestock.

30. The method of claim 4, wherein the RSV is a live purified RSV.

31. The method of claim 4, wherein the RSV is an attenuated RSV.

32. The method of claim 4, wherein the RSV is selected from the group consisting of bovine RSV, human RSV, and any combination thereof.

33. The method of claim 4, wherein the RSV is a human RSV.

34. The method of claim 4, wherein the RSV is bovine RSV.

35. The method of claim 4, further comprising administering one or more different oncolytic viruses, before, during and/or after administration of the RSV, wherein the one or more oncolytic viruses is selected from the group consisting of either nonengineered or engineered adenovirus, reovirus, herpesvirus, Newcastle disease virus, vaccinia virus, measles virus, Coxsackie virus, vesicular stomatitis virus, parvovirus, influenza virus, and Rabbit myxoma virus, and any combination thereof.

* * * * *